(12) United States Patent
Makower et al.

(10) Patent No.: US 11,304,793 B2
(45) Date of Patent: Apr. 19, 2022

(54) METHODS, SYSTEMS AND DEVICES FOR TREATMENT OF CEREBROSPINAL VENOUS INSUFFICIENCY AND MULTIPLE SCLEROSIS

(71) Applicant: Apertomed LLC, Mountain View, CA (US)

(72) Inventors: Joshua Makower, Los Altos Hills, CA (US); Earl A. Bright, II, Los Altos, CA (US); Theodore M. Bender, San Anselmo, CA (US); Joseph Catanese, III, San Leandro, CA (US); John Y. Chang, Los Altos, CA (US); Thomas King, Redwood City, CA (US); Clinton Slone, San Francisco, CA (US); Theodore C. Lamson, Pleasanton, CA (US); Aziz Imraan, Oakland, CA (US)

(73) Assignee: ExploraMed Development, LLC, Mountain View, CA (US)

( * ) Notice: Subject to any disclaimer, the term of this patent is extended or adjusted under 35 U.S.C. 154(b) by 233 days.

(21) Appl. No.: 16/264,842

(22) Filed: Feb. 1, 2019

(65) Prior Publication Data

US 2019/0167410 A1 Jun. 6, 2019

Related U.S. Application Data

(63) Continuation of application No. 13/578,555, filed as application No. PCT/US2011/024094 on Feb. 8, 2011, now abandoned.

(Continued)

(51) Int. Cl.
*A61F 2/06* (2013.01)
*A61F 2/915* (2013.01)
(Continued)

(52) U.S. Cl.
CPC ............... *A61F 2/06* (2013.01); *A61F 2/915* (2013.01); *A61F 2/885* (2013.01); *A61F 2/89* (2013.01);
(Continued)

(58) Field of Classification Search
CPC ...... A61F 2/06; A61F 2/07; A61F 2/82; A61F 2/844; A61F 2/852; A61F 2/856;
(Continued)

(56) References Cited

U.S. PATENT DOCUMENTS 5,344,425 A * 9/1994 Sawyer ............... A61F 2/88
600/36
6,350,277 B1 * 2/2002 Kocur ............... A61F 2/90
623/1.11
(Continued)

*Primary Examiner* — Tan-Uyen T Ho
*Assistant Examiner* — Chima U Igboko

(57) ABSTRACT

Methods and devices for relieving stenoses in, or otherwise improving blood flow through, body lumens. Although applicable in a variety of different body lumens, the methods and devices of this invention are specifically useable for relieving stenoses in, or otherwise improving blood flow through, veins which drain blood from the brain for treatment of multiple sclerosis or other neurodegenerative disorders that are caused, triggered or exacerbated by venous occlusion or venous insufficiency.

16 Claims, 29 Drawing Sheets

Related U.S. Application Data

(60) Provisional application No. 61/303,274, filed on Feb. 10, 2010.

(51) Int. Cl.
*A61F 2/88* (2006.01)
*A61F 2/89* (2013.01)
*A61F 2/82* (2013.01)

(52) U.S. Cl.
CPC . *A61F 2002/825* (2013.01); *A61F 2220/0008* (2013.01); *A61F 2220/0016* (2013.01); *A61F 2230/0054* (2013.01)

(58) Field of Classification Search
CPC .... A61F 2/86; A61F 2/88; A61F 2/885; A61F 2/89; A61F 2/90; A61F 2/91; A61F 2/92; A61F 2/93; A61F 2/94; A61F 2/945; A61F 2/915; A61F 2002/072; A61F 2002/075; A61F 2002/077; A61F 2002/821; A61F 2002/823; A61F 2002/825; A61F 2002/826; A61F 2002/828; A61F 2002/9505; A61F 2002/9511; A61F 2002/9534; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583; A61F 2002/91591; A61F 2230/0054

See application file for complete search history.

(56) References Cited

U.S. PATENT DOCUMENTS

| | | | |
|---|---|---|---|
| 2005/0065592 A1* | 3/2005 | Holzer | A61F 2/07 623/1.13 |
| 2010/0161033 A1* | 6/2010 | Jantzen | A61F 2/07 623/1.16 |
| 2011/0060401 A1* | 3/2011 | Hoerstrup | A61L 31/148 623/1.16 |

* cited by examiner

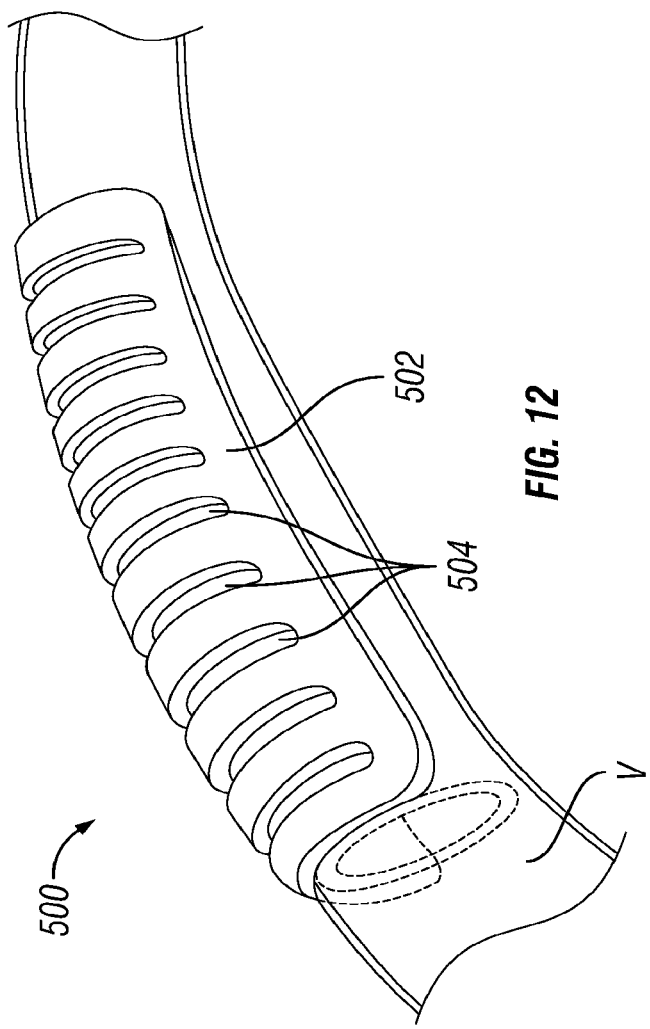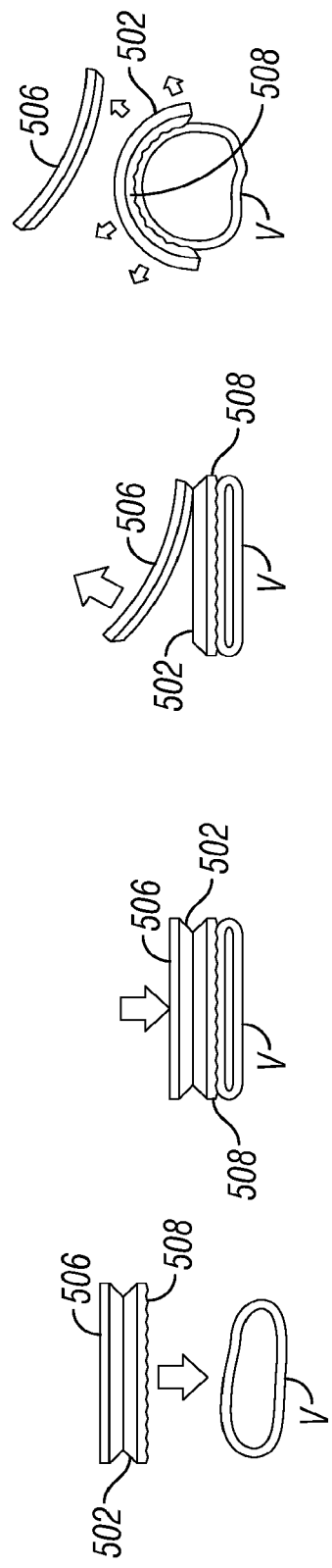

METHODS, SYSTEMS AND DEVICES FOR TREATMENT OF CEREBROSPINAL VENOUS INSUFFICIENCY AND MULTIPLE SCLEROSIS

RELATED APPLICATION

This application is a continuation of U.S. patent application Ser. No. 13/578,555 filed Oct. 15, 2012, which is a 35 U.S.C. § 371 national stage of PCT International Patent Application No. PCT/US2011/24094 entitled Methods, Systems and Devices For Treatment of Cerebrospinal Venous Insufficiency And Multiple Sclerosis filed Feb. 8, 2011, which claims priority to U.S. Provisional Patent Application Ser. No. 61/303,274 filed Feb. 10, 2010, the entire disclosures of said applications being disclosure of which is expressly incorporated herein by reference.

FIELD OF THE INVENTION

The present invention relates generally to biology and medicine and more particularly to methods, systems and devices for treating venous obstruction or venous insufficiency and for treatment of neurological or other disorders, such as multiple sclerosis (MS), which may be associated with venous obstruction or insufficiency.

BACKGROUND OF THE INVENTION

Pursuant to 37 CFR 1.71(e), this patent document contains material which is subject to copyright protection. The copyright owner has no objection to facsimile reproduction of the complete patent document or the patent disclosure, as it appears in the Patent and Trademark Office patent file or records, but otherwise reserves all copyright rights whatsoever.

Nerve cells of the central nervous system communicate with one another by transmitting electrical signals, known as action potentials, through long nerve fibers, known as axons. Each axon is sheathed in a layer of an insulating substance called myelin. Multiple sclerosis (MS) causes demyelination and scarring of the axons, which in turn results in impaired conduction of action potentials, neuroaxonal apoptosis and degeneration.

Although many risk factors for multiple sclerosis have been identified, no definitive cause has been found. MS is difficult to diagnose in its early stages. There is no known cure for MS and the specific pathophysiology by which MS progresses is not fully understood.

MS is not considered a hereditary disease but certain genetic variations are associated with increased risk of developing MS. Currently, MS is believed to be an immune-mediated disorder that occurs in response to some initial trigger. The nature of what triggers the onset of MS has been debated for many years. It is generally accepted that several clinically definable subtypes of MS exist, as follows:

Relapsing-Remitting: Relapsing-remitting describes the initial course of 85% to 90% of MS cases. This subtype is characterized by unpredictable attacks (relapses) followed by periods of months to years of relative quiet (remission) during which there are no new signs of disease activity. Deficits suffered during the attacks may either resolve or may be permanent. Cases where the deficits always fully resolve between attacks are referred to as "benign" MS.

Secondary Progressive: Around 80% of patients who initially suffer from relapsing-remitting MS will progress to a secondary progressive form of the disease wherein they exhibit neurologic decline between their acute attacks without any definite periods of remission. This neurologic decline may include new neurologic symptoms, worsening cognitive function, or other deficits. Secondary progressive is the most common type of MS and causes the greatest amount of disability.

Primary Progressive: Primary progressive describes the approximately 10% of individuals who never have remission after their initial MS symptoms. Decline occurs continuously without clear attacks. The primary progressive subtype tends to affect people who are older at disease onset.

Progressive Relapsing: In the progressive relapsing form of MS, patients exhibit a steady neurologic decline but also suffer superimposed attacks.

The blood-brain barrier normally prevents T lymphocytes and other elements of the blood form entering neural cells of the central nervous system. However, when the blood-brain barrier is broken (as sometimes occurs in certain viral infections), T lymphocytes and other elements of the blood can cross the blood-brain barrier into neural cells. The patient's immune system can then activate those T lymphocytes, causing autoimmune damage to the neural cells. It is on this basis that some investigators suggest that viral infections may trigger MS.

Investigators have previously reported ultrasound and venographic data indicating that chronic cerebrospinal venous insufficiency (CCVI) may cause elevated cerebral venous pressure in many MS patients. In these patients, the CCVI appears to be caused by stenosis of the jugular and/or azygous and/or lumbar veins. Zamboni, P., et al.; *Chronic Cerebrospinal Insufficiency in Patients with Multiple Sclerosis*, J Neurol. Neurosurg. Psychiatry; 80 (4) 392-399 (2009) (published on line Dec. 5, 2008). It is postulated that the elevated cerebral venous pressure may cause certain blood components to transgress the blood-brain barrier, thereby triggering an inflammatory and/or immune response in neural tissue located around veins or venules. A non-randomized pilot study has indicated that percutaneous transluminal angioplasty can be used to dilate the stenotic veins and that improvement of MS symptoms may result. However, this initial study, the devices and techniques employed were generally designed for treatment of other types of obstructions in other lumens of the body and, thus, are less than optimal for use in this application. Zamboni P, et al.; *A Prospective Open-Label Study of Endovascular Treatment of Chronic Cerebrospinal Venous Insufficiency*; J Vasc. Surg. 50:1348-1358 (2009).

Also, other investigators have failed to confirm any increased incidence of CCVI in MS patients. See, Sundström, P., et al.; *Venous and Cerebrospinal Fluid Flow In Multiple Sclerosis: A Case-Control Study*; Ann. Neurol. 68 (2): 255-259 (2010); Doepp, F., et al. *No Cerebrocervical Venous Congestion in Patients With Multiple Sclerosis*; Ann. Neurol. 68 (2): 173-83 (2010).

More definitive studies are ongoing to assess whether, or to what extent, a relationship exists between CCVI and MS and, if so, how best to treat CCVI. In particular, investigators are assessing whether angioplasty without stenting is an adequate treatment for CCVI or whether some stenting is required to ensure continued patency of the veins following angioplasty. One recent publication has reported that the re-stenosis rate following angioplasty without stenting was unacceptably high (approximately 50% for internal jugular vein occlusions) and that such re-stenosis was often accompanied by worsening neurological symptoms. This publication concluded that stenting is probably the easiest and safest way to avoid re-stenosis following angioplasty for CCVI, but also recognized that a) the most probable serious complication of venous stenting following angioplasty for CCVI is migration of the stent to the heart or into the pulmonary circulation, b) the increased potential for stent migration in veins is due in part to the fact that veins normally dilate and contract in response to changes in proximal and distal flow resistances and changes in the level of external compression and gravitational forces and c) to avoid potentially life threatening stent migration ion CCVI cases, the stent must be precisely tailored to the blood vessel. Ludyga, T. et al.; *Safety of Endovascular Treatment For CCSVI*; Phlebology; 25:286-295 (2010).

Most of the vascular stents of the prior art have been used for stenting obstructed arteries, not veins. However, stenting of veins has been performed since at least the late 1980's. Zollikofer, C. et al., *Endovascular Stenting of Veins and Grafts: Preliminary Clinical Experience; Radiology* 1988, 167:707-712. Stenting is thought to act as an adjuvant to venous angioplasty by limiting the elastic recoil in compliant veins, excluding the damaged and dissected vasculature and counteracting extrinsic compression. Both balloon-expandable stents and self-expandable flexible stents have been implanted in central venous stenoses. Haage, P, et al.; *Treatment of Haemodialysis Related Central Venous Stenosis Or Occlusion: Results of Primary Walilstent Placement And Follow Up In* 50 *Patients; Radiology* 1999, 212:175-180. However, because they generally conform better to the shape of the venous wall, self-expanding stents have been reported to be preferable for restoring venous patency and self-expanding stents that have the ability to diametrically self-adjust following implantation are viewed as advantageous for use in veins that undergo dilation or enlargement after stent deployment. Vorwerk, D, et al.; *Venous Stenosis And Occlusion In Haemodialysis Shunts: Follow Up Results Of Stent Placement In* 65 *Patients*; Radiology 1995, 195: 140-146. Generally, use of these stents is less than optimal because a number of adverse complications can occur.

The prior art has included a relatively small number of stents designed specifically for venous applications. For example, U.S. Pat. No. 5,851,232 (Lois) entitled Venous Stent describes a stent assembly that includes a cylindrical shell and a plurality of circular coils embedded within the cylindrical shell which is purportedly useful as a venous stent due to its physical characteristics. The entire disclosure of U.S. Pat. No. 5,851,232 (Lois) is expressly incorporated herein by reference. Also, various valved venous stents for treating chronic venous insufficiency of the lower extremities have been disclosed, including those described in United States Patent Application Publication Nos. 2009/0254175 (Quijano, et al.) entitled Valved Stent for Chronic Venous Insufficiency and 2002/0138135 (Duerig, et al) entitled Stent-Based Venous Valves, the entire disclosures of which are expressly incorporated herein by reference.

None of the existing methods, devices or systems are believed to be optimal for treating all cases of chronic cerebrospinal venous insufficiency in MS patients. There is an absence in the market of dedicated devices of the proper size, length and functional characteristics for treating CCVI. Using existing stents at the level of the internal jugular vein and/or azygous vein creates risk of displacement, migration along the vein, stenosis, thrombosis, thromboembolism, migration thru and/or perforation of the venous wall and pulmonary migration, thus affecting venous outflow. Accordingly, there remains a need in the art for the development of new methods, devices and systems for the treatment of chronic cerebrospinal venous insufficiency in MS patients.

SUMMARY OF THE INVENTIONS

In accordance with the present invention, there are provided various methods and devices for relieving stenoses in, or otherwise improving blood flow through, body lumens. Although applicable in a variety of different body lumens, the methods and devices of this invention are specifically useable for relieving stenoses in, or otherwise improving blood flow through, veins which drain blood from the brain for treatment of MS or other neurodegenerative disorders that are caused, triggered or exacerbated by elevated cerebral venous blood pressure and other diseases caused by primary or secondary venous insufficiency such as irritable bowel syndrome. In accordance with the methods and devices of the present invention, the pressure upstream and downstream of the stenosis is equalized.

Unless otherwise specifically noted, the term "stenosis" is used throughout this application to refer to any full or partial blockage or restriction of flow through a body lumen, including but not limited to full or partial blockages or restrictions of flow caused by narrowing of the body lumen, such as being twisted or having sharp reductions in diameter due to malformation, or by the presence of obstructive matter within the body lumen.

The present invention includes endovascular devices/methods, exovascular devices/methods and surgical devices/methods for improving blood flow through stenotic regions of body lumens. In some embodiments, the body lumen is the lumen of a stenotic cerebrospinal vein (such as the azygous or right or left internal jugular vein) in a subject who suffers from MS or another neurodegenerative disorder.

In accordance with one aspect of the present invention, there are provided endovascular devices that are implanted within a stenotic region of a body lumen, such stent devices being modifiable (e.g., "tunable") following initial implantation to optimize their efficacy and minimize untoward effects. For example, the present invention includes endovascular stents that are a) initially constrainable in a collapsed configuration having a first diameter suitable for advancement into the stenotic region of the body lumen, b) self-expandable to a second diameter when unconstrained and c) further pressure-expandable in whole or in part to diameter(s) larger than the second diameter. Such stents are of a suitable design and construction. For example, in one embodiment, such stent comprises one or more self-expanding components (e.g., zig-zag, mesh ring(s), helical members, braided sections, etc.) with one or more plastically deformable constraining member(s) (e.g., stretchable filaments) connected thereto. The plastically deformable constraining member(s) initially constrain the stent so that it cannot self-expand beyond the second diameter. Thereafter, if it is desired to further expand all or, importantly, specific region(s) of the stent beyond the second diameter, a balloon or other expandable member may be positioned within the stent and used to plastically deform one or more of the constraining member(s) to further expand the stent (or selected region(s) thereof) to at least a third diameter which is larger than the second diameter. The stent is up-sized in specific regions so that it fully opposes the wall of the vein along the length of the stent and provides anchoring sections in which the up-sized regions are upstream or downstream of narrow venous sections such that under sizing does not occur as is common with conventional stents.

In accordance with another aspect of the present invention, there are provided methods for improving fluid flow through a stenotic body lumen of a human or mammalian subject (e.g., the lumen of a vein in a patient suffering from CCVI, MS or another neurodegenerative disease), such methods comprising the step of placing an endovascular or exovascular device in or near the stenotic body lumen and at least one additional step selected from the group consisting of:

a) imaging or measuring the stenotic body lumen and, prior to placing the device, customizing at least part of the device to correspond to the image or measurements of the body lumen;
b) initially expanding the device to a first expanded configuration and, thereafter, further expanding all or part(s) of the device to conform to the anatomy of the stenotic body lumen;
c) causing the device to communicate with one or more sensors such that the device will exert varying force of the stenotic body lumen in response to information received from the one or more sensors;
d) placing a plurality of said devices at separate locations corresponding to the anatomy and/or locations of stenotic regions of the body lumen;
e) causing the device to pump body fluid through the body lumen;
f) forming a full-thickness or partial-thickness cut in or through a wall of the body lumen to relieve constraint or stricture or to otherwise widen the body lumen;
g) tuning (e.g., modifying, adjusting shape, adjusting size, etc.) the device after it has been placed in or near the body lumen;
h) delivering from the device or by other means an active substance for providing some desired therapeutic effect; and
i) causing the device or some other means to cause muscle to relax or expand thereby decreasing muscle compression of the stenotic body lumen In accordance with yet another aspect of the present invention, there are provided methods for treating stenosis of a body lumen in a human or animal subject (e.g., the lumen of a vein in a patient suffering from CCVI, MS or another neurodegenerative disease), comprising the steps of: inserting into the body lumen a stent device that comprises a self-expanding portion and at least one deformable constraining member, said stent device being in a collapsed configuration; allowing the self expanding portion to self-expand from the collapsed configuration to a first expanded configuration; and, pressure-deforming at least one deformable constraining member to modify the shape and/or diameter of the stent device. In some embodiments, the self-expanding portion comprises a generally tubular body and the at least one deformable constraining member comprises a member that extends at least part way around the generally tubular body to deter its expansion beyond the first expanded configuration and deforming such constraining member(s) will allow at least part of the generally tubular body to expand to a diameter that is larger than its diameter when in the first expanded configuration.

In accordance with yet another aspect of the present invention, there is provided a stent device comprising at least one self-expanding stent member and at least one deformable constraining member connected to the at least one self-expanding stent member, wherein the self-expanding stent member(s) is/are initially deployable in a collapsed configuration thereafter self-expandable to a first expanded configuration and the at least one plastically deformable constraining member is initially operative to constrain the at least one self-expanding stent member so that it does not self expand beyond the first expanded configuration but thereafter deformable, in whole or in part, to a deformed configuration that allows some or all of the self-expanding stent member(s) to further expand to a second expanded configuration. In some embodiments, the self-expanding stent member(s) comprise one or more self-expanding rings (e.g., the rings may be of zig zag, mesh, coil or any other suitable stent construction).

In accordance with yet another aspect of the present invention, there are provided methods for improving flow through a stenotic body lumen in a human or animal subject (e.g., the lumen of a vein in a patient suffering from CCVI, MS or another neurodegenerative disease), comprising the step of delivering energy to a wall of the stenotic body lumen or to tissue located near the stenotic body lumen or to obstructive matter located within the stenotic body lumen to cause shrinkage, contraction or other movement of tissue or obstructive matter in a manner that improves fluid flow or equalization of pressure through the stenotic body lumen. The energy is delivered from a catheter or other delivery device that is outside or inserted into the body lumen or from an endovascular or exovascular device implanted within or near the body lumen. The energy comprises any suitable type of energy including but not limited to heat, light, laser light, infrared light, a plasma field, sound, ultrasound, electromagnetic radiation and ionizing radiation.

In accordance with yet another aspect of the present invention, there are provided methods for improving flow through a stenotic body lumen in a human or animal subject (e.g., the lumen of a vein in a patient suffering from CCVI, MS or another neurodegenerative disease), comprising the step of delivering a quantity of material (e.g., a gel or foam) to a location within the subject's body so that the material exerts force(s) which enlarge the stenotic body lumen or deter compression or contraction of the stenotic body lumen (e.g., shield the vein so that forces of muscular contraction do not cause the vein to collapse). In some embodiments, the material may undergo a change in volume or shape after it has been delivered. For example, the material may contract (e.g., shrink) in situ so as to pull on adjacent tissue, causing enlargement of the stenotic body lumen.

In accordance with yet another aspect of the present invention, there are provided methods for improving flow through a stenotic body lumen in a human or animal subject (e.g., the lumen of a vein in a patient suffering from CCVI, MS or another neurodegenerative disease), comprising the step of implanting within the body lumen a device that comprises two or more strut members extending between two or more radially expandable ring or partial-ring members.

In accordance with yet another aspect of the present invention, there is provided a device comprising: a first full or partial ring member, a second full or partial ring member and at least two strut members connected to and extending between the first and second ring members. Such device is deliverable into a stenotic body lumen while in a collapsed configuration and subsequently transitionable to an expanded configuration whereby it widens the stenotic body lumen.

In accordance with yet another aspect of the present invention, there are provided methods for improving flow through a stenotic body lumen in a human or animal subject (e.g., the lumen of a vein in a patient suffering from CCVI, MS or another neurodegenerative disease), comprising the step of implanting magnets at locations in or near the stenotic body lumen. For example, the magnets are positioned on opposite sides of the body lumen and repel one another so as to dilate the body lumen.

In accordance with yet another aspect of the present invention, there are provided methods and devices for implanting an implantable device within a stenotic region of a body lumen by inserting into the body lumen a delivery device having a distal end, an implantable device delivery location from which the implantable device is deliverable and a locator member (e.g., a balloon) immediately distal to the device delivery location, such locator being transitionable back and forth between a collapsed configuration wherein it can pass through the stenotic region and an expanded configuration wherein it will not pass through the stenotic region; advancing the delivery device, distal-end-first, through the stenotic region with the locator member in a collapsed configuration; expanding the locator member to an expanded configuration; retracting the delivery device until the expanded locator member abuts against the stenotic region, thereby indicating that the delivery location is within the stenotic region; delivering the implantable device from the delivery location so that it becomes implanted in the stenotic region; causing the locator member to transition from the expanded configuration to a collapsed configuration and withdrawing the delivery device, leaving the implantable device implanted within the stenotic region.

In accordance with yet another aspect of the present invention, there are provided methods for treating two or more stenotic regions at spaced-apart locations in a body lumen, said method comprising the steps of: delivering into the body lumen a device that comprises two or more expandable members connected by one or more linear elements, the distance between the expandable members being substantially the same as the luminal distance between the stenotic regions; positioning the expandable members within the stenotic regions with the linear elements extending through the body lumen between the stenotic regions; and expanding the expandable members such that they dilate the stenotic regions.

In accordance with yet another aspect of the present invention, there are provided methods and apparatus whereby endovascular devices, such as stents, are prevented or deterred from moving or migrating from a desired implantation site within a blood vessel. In some embodiments, the endovascular device may comprise a radially expandable (e.g., self-expanding or pressure-deformable) scaffold member with incorporated or associated means (e.g., apparatus, materials, attributes and/or operational features) for deterring unwanted movement or migration after implantation. The means (e.g., apparatus, materials, attributes, operational features and/or method steps) which may be incorporated in, associated with or used in an endovascular device to deter unwanted movement or migration of the endovascular device include but are not limited to; a) protrusions, members, hooks, barbs, ridges, surface features, bumps, or other projections or members on the endovascular device that enter, embed in, penetrate and/or frictionally engage the wall of the blood vessel in which the endovascular device is positioned, b) magnets on the endovascular device and/or in the blood vessel wall and/or outside of the blood vessel which create a magnetic attraction to deter unwanted migration or movement of the endovascular device, c) adhesives, tissue glues or other materials which cause the endovascular device to adhere to or remain in contact with the adjacent blood vessel wall, d) the application of endothelial seeking, growth factors, cells, cell growth promoters or fenestrations, passageways or surface features into or onto which tissue (e.g., endothelium) may grow such that the endovascular device or any part thereof becomes encapsulated, overgrown, covered, fully or partially surrounded or otherwise engaged by cells or tissue (e.g., endothelial tissue) in a manner which deters its unwanted movement or migration and/or e) design/radial expansion attributes of the device and/or method steps during implantation of the device which cause the device to remain in sufficient abutment or engagement with the blood vessel wall to deter its unwanted movement or migration, including in cases where implanted in a vein or capacitance vessel, the ability of the device to expand and remain in coaptation or abutment with the vein wall even when the vein undergoes physiological dilation or radial expansion.

Still further aspects and details of the present invention will be understood upon reading of the detailed description and examples set forth herebelow.

BRIEF DESCRIPTION OF THE DRAWINGS

The drawings and the associated descriptions are provided to illustrate embodiments of the invention and not to limit the scope of the invention. Throughout the drawings, reference numbers are re-used to indicate correspondence between referenced elements.

FIG. 12 shows an exovascular device of the present invention positioned to deter collapse or support the wall of a vein so as to maintain the vein in an open, non-stenotic configuration.

FIGS. 12A through 12D show steps in a method for implantation and use of the device of FIG. 12.

DETAILED DESCRIPTION OF THE INVENTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Figure 1A:
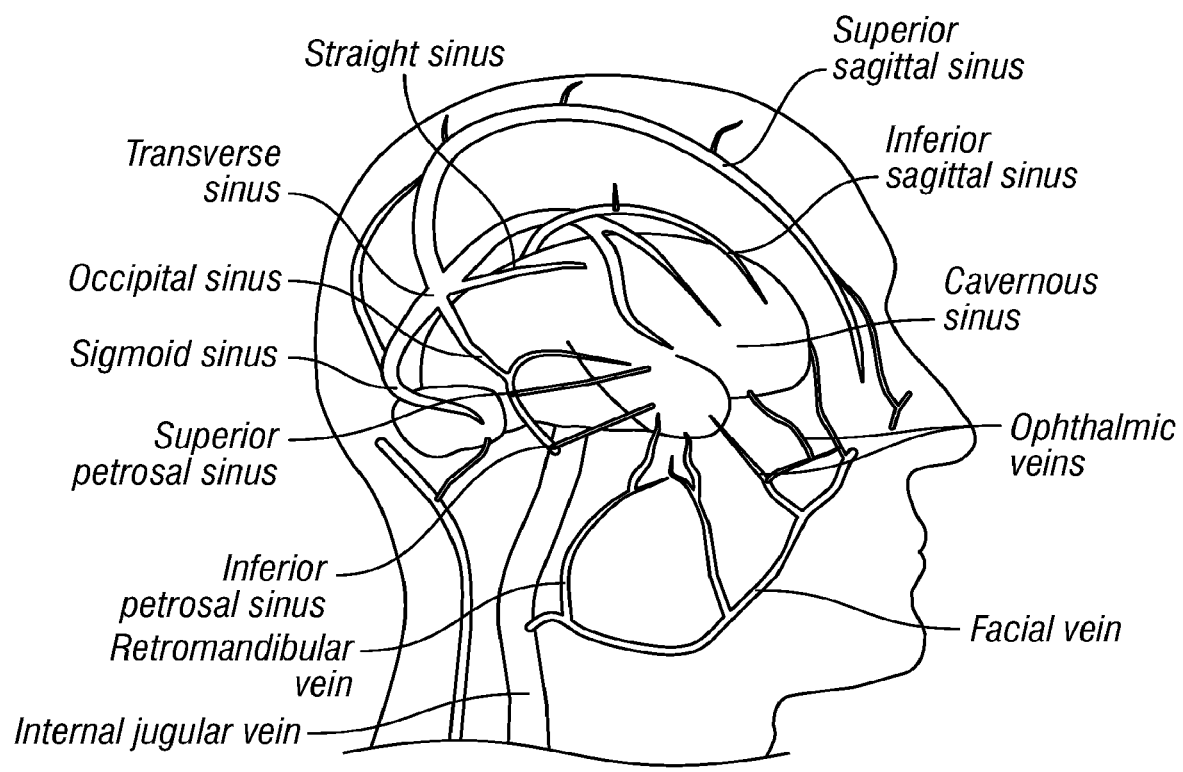
FIG. 1A is a schematic diagram of the major veins of the human brain.
Figure 1B:
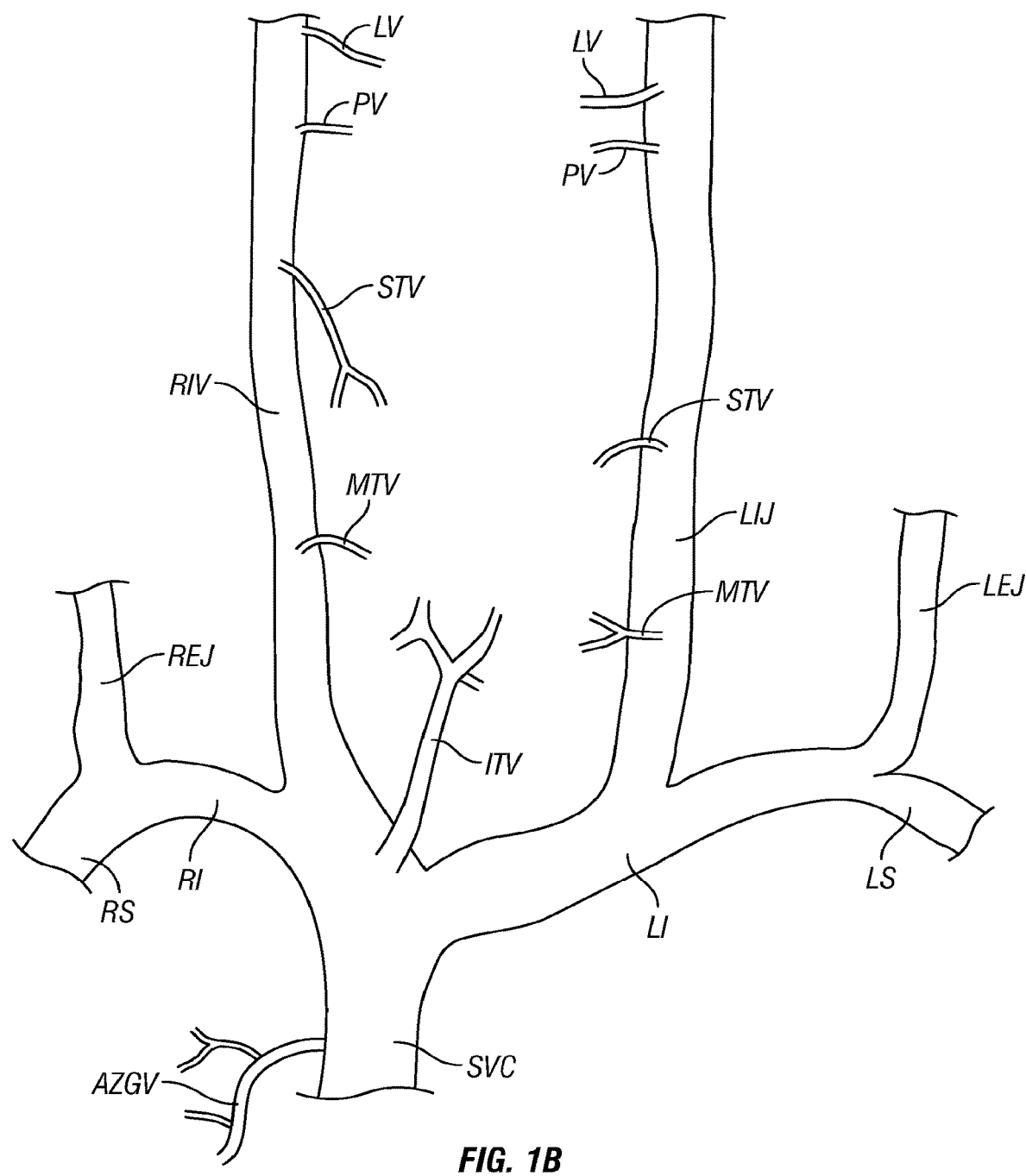
FIG. 1B is a schematic diagram showing major veins of the neck and upper thorax through which venous blood drains from the brain.

FIG. 1A is a schematic diagram of the major veins of the human brain with the names of specific veins labeled thereon. FIG. 1B is a schematic diagram showing major veins of the neck and upper thorax through which venous blood drains from the veins of the brain. Reference letters are used to indicate specific veins, as follows:

| Label | Vessel |
| --- | --- |
| SVC | Superior Vena Cava |
| RI | Right Inominate |
| LI | Left Inominate |
| RS | Right Subclavian |
| LS | Left Subclavian |
| RIJ | Right Internal Jugular |
| LIK | Left Internal Jugular |
| REJ | Right External Jugular |
| LEJ | Left External Jugular |
| ITV | Inferior Thyroid Veins |
| MTV | Middle Thyroid Veins |
| STV | Superior Thyroid Veins |
| PV | Pharyngeal Veins |
| LV | Lingual Veins |

Patients who suffer from CCVI often have one or more stenotic regions in the azygous vein (AZYV) or right and/or left internal jugular veins LIV, RIV. As may be noted from the diagram of FIG. 1B, it is typically desirable to treat stenotic regions of the azygous vein or right and/or left internal jugular veins LIV, RIV to avoid obstruction of flow into the internal jugulars from tributary veins such as the various thyroid veins STV, MTV, ITV, the pharyngeal veins PV and/or the lingual veins LV It is also desirable to treat the LIV, RIV, and/or AZYV in order to reduce pressure gradients that exist due to the development of many small diameter collateral veins that have developed.

Figure 2A:
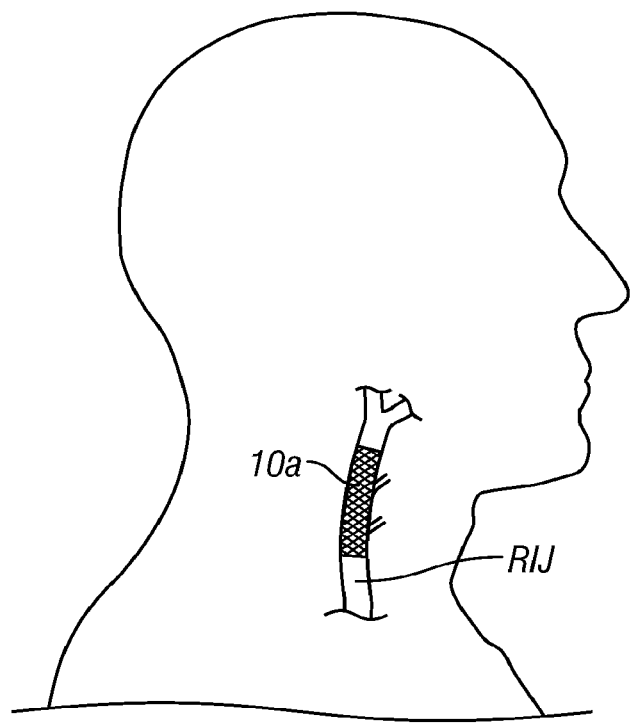
FIG. 2A is a schematic diagram which generally shows an endovascular apparatus of the present invention implanted within a stenotic region of an internal jugular vein of a human subject.
Figure 2B:
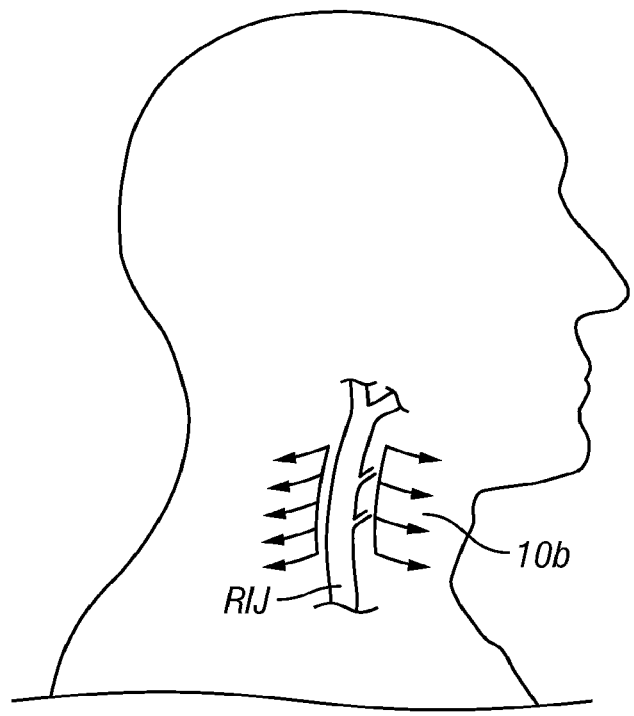
FIG. 2B is a schematic diagram which generally shows an exovascular apparatus of the present invention implanted within the neck of a human subject adjacent to a stenotic region of an internal jugular vein.

The present invention includes endovascular devices/methods as well as exovascular devices/methods and surgical procedures. FIG. 2A generally shows an endovascular device 10a of the present invention implanted within a stenotic region of a right internal jugular vein RIJ of a human subject. This endovascular device 10a can comprise a stent, scaffold, pump, valve or other device that facilitates blood flow through the stenotic region to equalize the pressure upstream and downstream of the stenotic region, specific examples of which are described below. FIG. 2B generally shows an exovascular device 10b of the present invention implanted within the neck of a human subject adjacent to a stenotic region of the right internal jugular vein RIV. This exovascular device 10b can comprise an exovascular stent, shell, vessel dilator, pump or other device that facilitates blood flow through the stenotic region, specific examples of which are described below. The endovascular devices 10a and exovascular devices 10b can be used separately or in combination. In some embodiments, these endovascular devices 10a and exovascular devices 10b are constructed to maintain substantially constant diameter or other effect(s) on the vein, thereby resulting in substantially constant dilation of, or other facilitation of blood flow and pressure equalization through, the vein. In other embodiments, these endovascular devices 10a and exovascular devices 10b are constructed to have a non-continuous (e.g., interrupted, cyclic or occasional) diameter(s) or other effect(s) on the vein, thereby resulting in facilitation of blood flow through the vein. In such embodiments where the device 10a or 10b applies interrupted, cyclic or occasional force or other effect(s) on the vein, the devices can include one or more sensors which sense physiological, temporal, postural or other variables or events and a microprocessor or other apparatus that actuates the device only when certain triggering variables or events are detected. For example, the device can be actuated when venous pressure exceeds a predetermined amount at certain location (e.g., upstream of the device) or when the subject assumes a posture that causes venous pressure in the brain to elevate (e.g., lying down) or during specific portion(s) of the subject's respiratory cycle when venous backpressure in the brain is likely to rise (e.g., when intrathoracic pressure is within certain limits that affect venous outflow through the cerebrospinal veins). The types of apparatus (e.g., sensors and microprocessors) that would be incorporated into devices of this type to achieve these functions are commercially available and known in the art. Some non-limiting examples of sensors and related signal processing apparatus include but are not limited to those described in U.S. Pat. No. 4,180,059 (Tiep) entitled Method Of Measuring Intrathoracic Pressure; U.S. Pat. No. 5,069,222 (McDonald Jr.) entitled Respiration Sensor Set; U.S. Pat. No. 5,873,835 (Hastings, et al.) entitled Intravascular Pressure And Flow Sensor U.S. Pat. No. 6,449,509 (Park, et al.) entitled Implantable Stimulation Device Having Synchronous Sampling For A Respiration Sensor, U.S. Pat. No. 6,517,497 (Rymut, et al.) entitled Method And Apparatus For Monitoring Respiration Using Signals From A Piezoelectric Sensor Mounted On A Substrate; U.S. Pat. No. 7,472,601 (Tenerz et al.) entitled Sensor For Intravascular Measurements Within A Living Body, the entire disclosure of each such patent being expressly incorporated herein by reference.

Figure 3A:
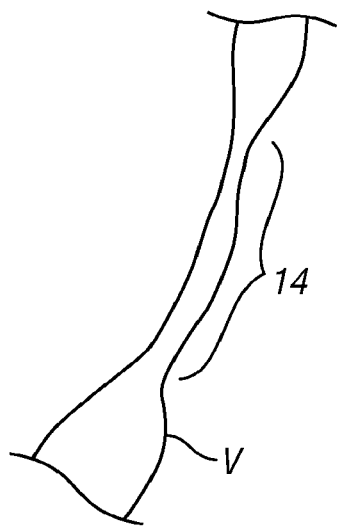
FIG. 3A shows a vein having a single elongate stenotic region.
Figure 3B:
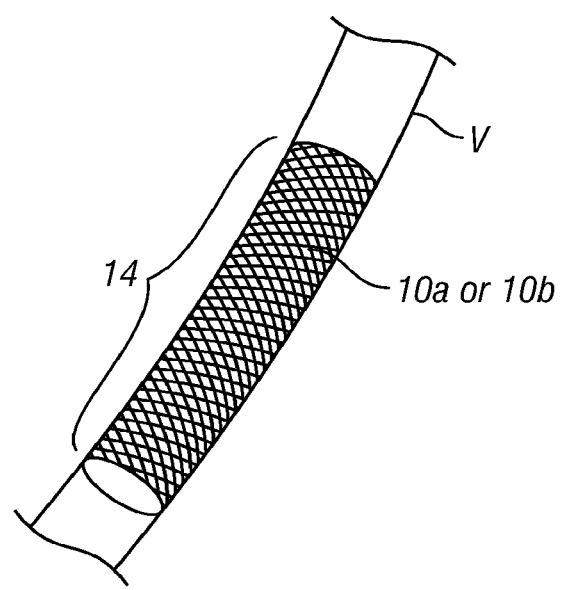
FIG. 3B shows the vein of FIG. 3A with a device of the present invention implanted so as to dilate the single stenotic region of the vein.
Figure 3C:
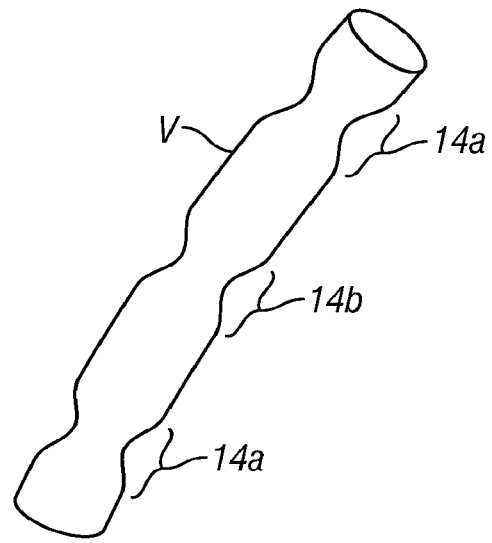
FIG. 3C shows a vein having a plurality of discrete stenotic regions.
Figure 3D:
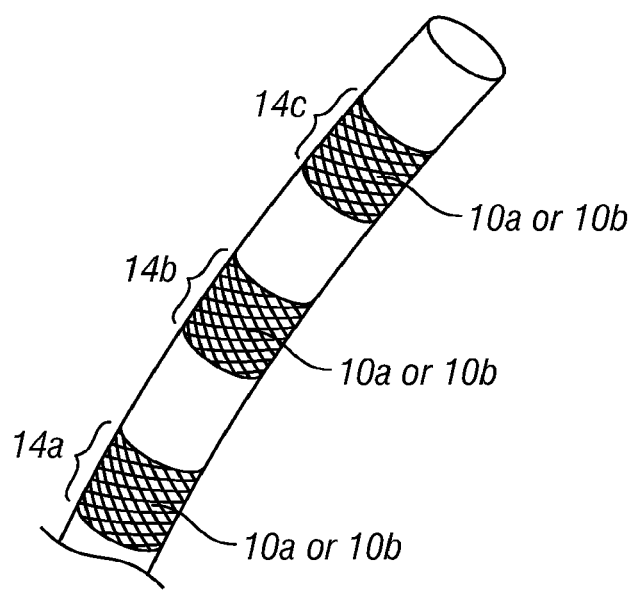
FIG. 3D shows the vein of FIG. 3C having a plurality of separate devices of the present invention implanted so as to dilate the discrete stenotic regions of the vein.
Figure 3E:
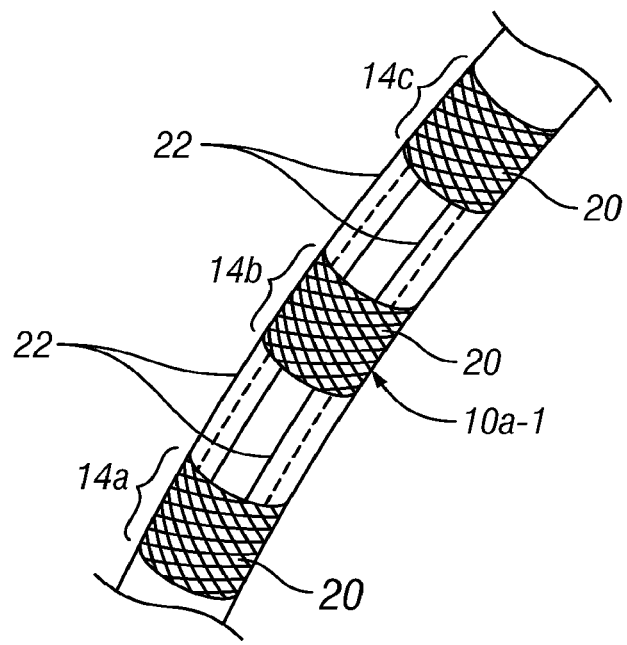
FIG. 3E shows the vein of FIG. 3C with a device of the present invention implanted therein, such device having a series of separate spaced-apart scaffolding ring members connected at spaced-apart locations by longitudinal linking members, such device being implanted such that the scaffolding ring members dilate each discrete stenotic region and the longitudinal members traverse the intervening non-stenotic regions of the vessel.
Figure 3F:
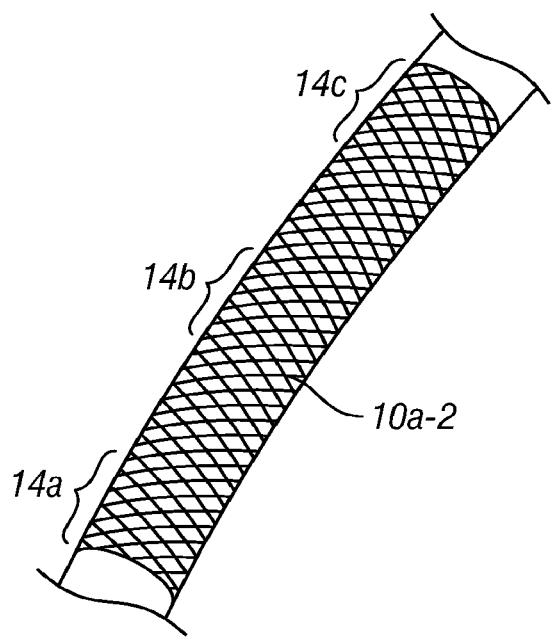
FIG. 3F shows the vein of FIG. 3C with a device of the present invention implanted so as to dilate/scaffold a continuous length of the vein that includes the discrete stenotic regions as well as the intervening non-stenotic regions.

The patterns of venous stenosis in CCVI may vary. In some subjects, a single stenotic region may be present while in other patients a plurality of small, discrete stenotic regions may be present with normal areas of vein in between. FIG. 3A shows an example of a vein V having a single elongate stenotic region 14. FIG. 3B shows a method wherein an endovascular device 10a or an exovascular device 10b of the present invention is implanted so as to dilate that entire stenotic region 14. FIG. 3C shows a vein V having a plurality of discrete stenotic regions 14a, 14b, 14c with unaffected, normal regions of vein therebetween. FIG. 3D shows a method wherein a plurality of separate devices 10a or 10b of the present invention are implanted so as to separately dilate the discrete stenotic regions of the vein without residing within or adversely affecting the unaffected, normal regions of vein therebetween. FIG. 3E shows the vein of FIG. 3C with an embodiment 10a-1 of an endovascular device of the present invention implanted therein. This endovascular device embodiment 10a-1 comprises a series of separate spaced-apart scaffolding members 20 connected by longitudinal linking members 22 such as wires or filaments. The scaffolding members can be not connected as well. The scaffolding members 20 can be self-expanding and/or pressure expandable, covered or uncovered, and are sized and constructed to dilate and stent the respective stenotic regions 14a, 14b, 14c of the vein V. The longitudinal linking members 22 comprise small diameter wires or filaments which, optionally, may be formed or formable to a desired curvature or shape and which serve to maintain the desired spacing distances between the scaffolding members 20 so that the scaffolding members will reside within the stenotic regions 14a, 14b, 14c. FIG. 3F shows the vein of FIG. 3C with an embodiment 10a-2 of an endovascular device of the present invention implanted therein. This endovascular device embodiment 10a-2 comprises a single, continuous scaffolding member (e.g., a stent) that is sized and implanted in the vein V such that it extends through all three stenotic regions 14a, 14b, 14c as well as the intervening non-stenotic regions of the vein located between the stenotic regions 14a, 14b, 14c.

Figure 4A:
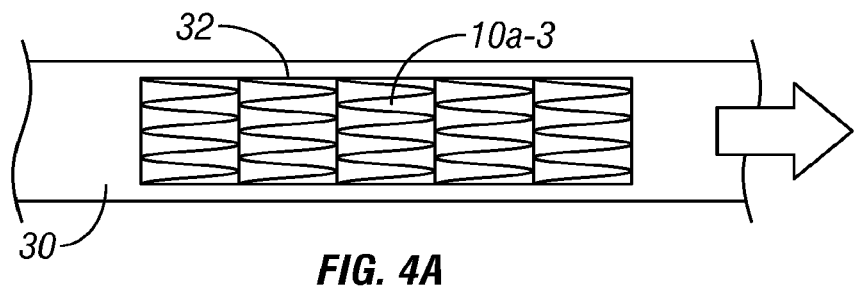
FIG. 4A shows a sheath deployable delivery system having one embodiment of an endovascular device of the present invention mounted thereon in a collapsed configuration.
Figure 4B:
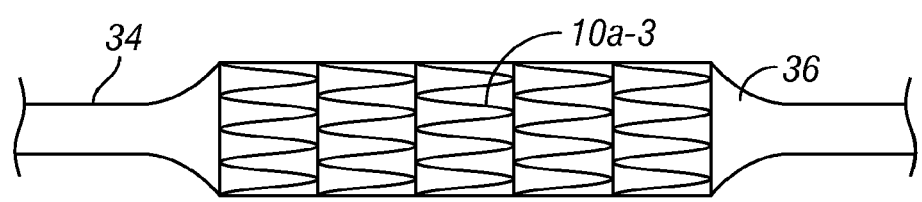
FIG. 4B shows a balloon deployable delivery system having one embodiment of an endovascular device of the present invention mounted thereon in a collapsed configuration.
Figure 4C:
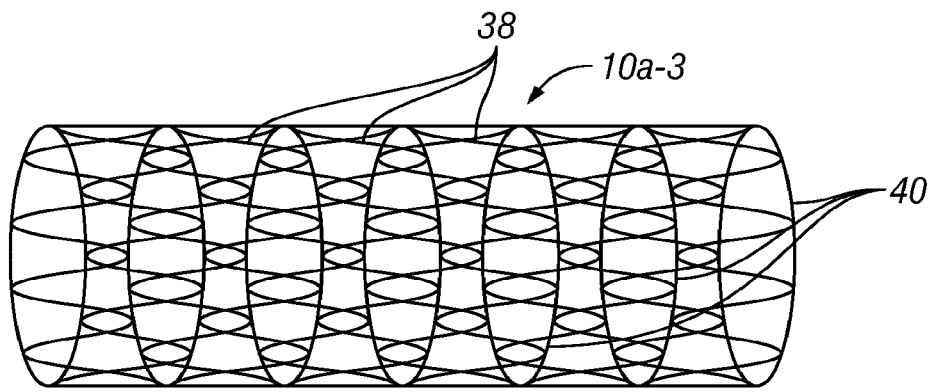
FIG. 4C shows one embodiment of an endovascular device of the present invention in a first expanded state.

FIGS. 4A through 4C show another endovascular device embodiment 10a-3 of the present invention. This embodiment 10a-3 is designed to self-expand to a first expanded diameter. Thereafter, all or portion(s) of the device can be further pressure-expanded to other diameter(s) to match the anatomy of the particular vein in which it is implanted. This embodiment 10a-3 is designed to: provide anchoring in the vein to prevent downstream migration, provide good scaffolding, have maximum flexibility, maintain close contact or association with the vein wall, minimize potential for thrombosis, maximize delivery flexibility during advancement and placement and provide for controlled release and deployment with minimal or no movement forward from the delivery system during deployment In general, this endovascular device embodiment 10a-3 comprises one or more self-expanding structures 38 and one or more plastically-deformable constraining members 40. In the particular example shown, the self-expanding structures 38 are zig-zag stents formed of a material that is sufficiently elastic to be constrained in an initial non-expanded configuration and, when unconstrained, will self-expand toward an expanded configuration (e.g., nickel-titanium alloy, self-expanding polymers, Elgiloy, chromium alloy, etc.). As an alternative to the zig-zag construction shown, the self-expanding structures 38 may comprise braided, mesh or woven members, helical wire coils or any other suitable stent construction. Also, in the particular example shown, each constraining member 40 comprises a filament or other member formed of plastically deformable metal or polymeric material (e.g., steel, expanded polytetrafluoroethylene (ePTFE), polymer, weave or other stretchable material) that is interlaced through the curves of the adjacent zig-zag self-expanding structures 38 or otherwise attached to the self-expanding structures 38 so as to link the self-expanding structures 38 together in series, as shown and limit each self-expanding structure 38 to expand to a first diameter.

FIG. 4A shows an example of how this endovascular device embodiment 10a-3 is initially delivered into a stenotic vein while mounted on a delivery catheter 30 in a collapsed configuration and constrained by a moveable sheath or other member 32. When positioned at the desired location within the vein, the moveable sheath or other member 32 is withdrawn, thereby allowing the self-expanding structures 38 to self-expand to the maximum extent allowed by the constraining members 40. Thereafter, as seen in FIG. 4B, one or more balloon(s) 36 of a separate balloon catheter 34 (or balloon(s) that were present under the device on the original delivery catheter 30) are used to further expand and plastically deform some or all of the constraining members 40 in the portions and to the diameter needed to alleviate the stenotic constriction and to make contact with the venous wall in the portions without stenotic constriction. In some applications, a balloon 36 having a constant diameter over its length is used to expand the embodiment 10a-3 to a diameter as shown in FIG. 4C. In other applications, the balloon 36 has a non-uniform shape (e.g., wide areas and narrow areas) or may comprise a series of individual balloons or a series of separate inflation chambers within a single balloon, to allow for regionalized variation in the amount of further expansion. In some applications, this endovascular device embodiment 10a-3 (as well as any other embodiment of the invention) and the balloon(s) (or the inflation pressures used in specific balloons or balloon compartments) are customized to match the anatomy of an individual stenotic vein in the manner illustrated in FIGS. 7A-7C and described herebelow. The endovascular device is released to a base diameter and then upsized in locations where necessary to achieve better fit and apposition to the venous wall. A series of balloon shapes and sizes can be used to create a desired fit.

Figure 4D:
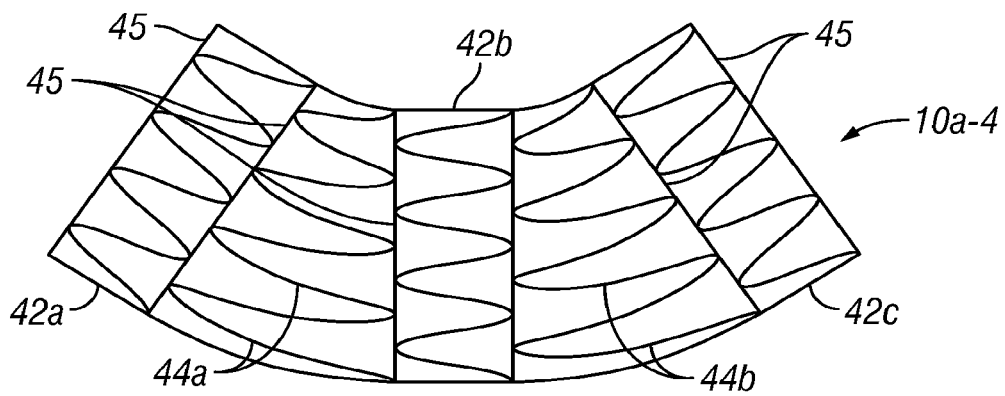
FIG. 4D shows another embodiment of an endovascular device of the present invention in a first expanded state and in a curved configuration.

FIG. 4D shows another embodiment 10a-4 of an endovascular device of the present invention which comprises a plurality of self-expanding structures 42a, 42b, 42c, a plurality of plastically deformable constraining members 45 and a plurality of linking members 44a, 44b which extend between the self-expanding structures 42a, 42b, 42c. The self-expanding structures 42a, 42b, 42c of this embodiment 10a-4 can be of the same construction as the self-expanding structures 38 of above-described embodiment 10a-3. Also, the plastically deformable constraining members 45 of this embodiment 10a-4 can be of the same construction as the plastically-deformable constraining members 40 of above-described embodiment 10a-3. The linking members 44a, 44b may be flexible or rigid members depending on the intended application. In the embodiment shown, the linking members 44a, 44b are thin members formed of any suitable material (e.g., metal, ePTFE, nickel-titanium alloy). In this particular embodiment, the linking members comprise thin, straight, flexible wires that run diagonally between adjacent ones of the expandable members 42a, 42b and 42c, allowing for flexibility and bending of the embodiment 10a-4 so that it may assume a desired curved shape, as shown in FIG. 4D.

Figure 4E:
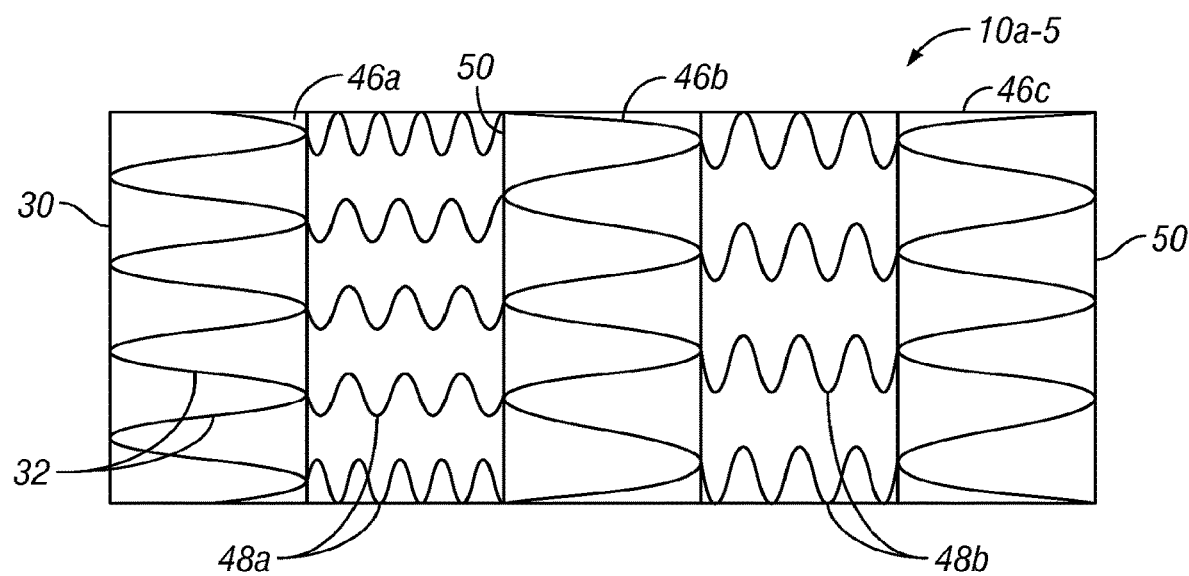
FIG. 4E shows another embodiment of an endovascular device of the present invention in a first expanded state.
Figure 4F:
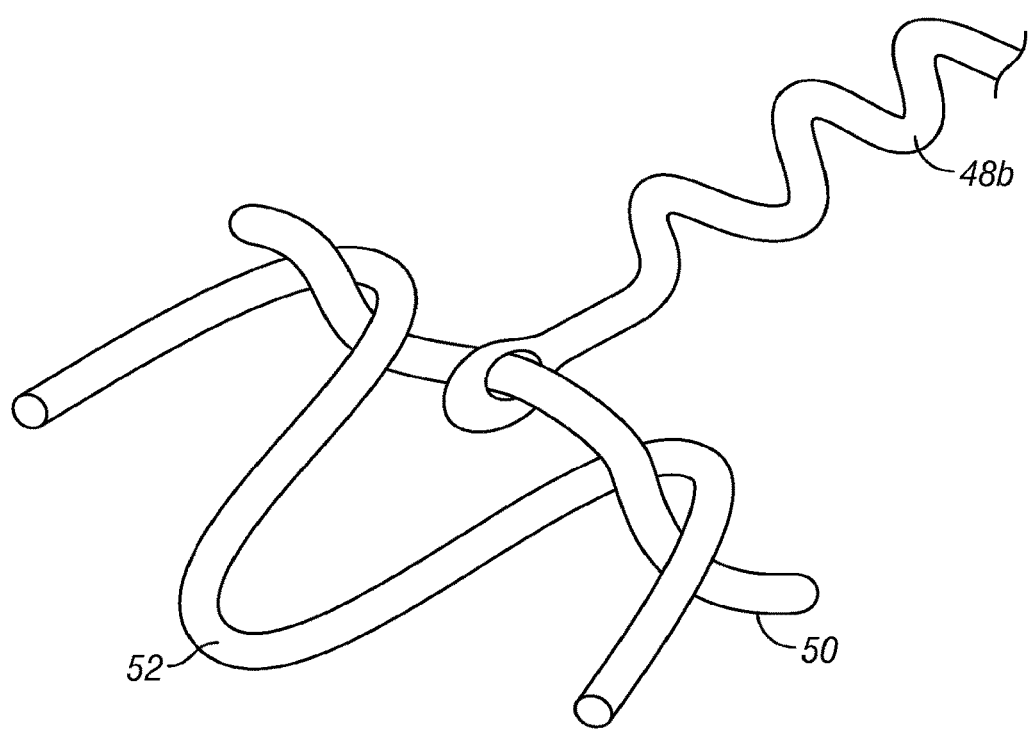
FIG. 4F is an exploded view of a portion of the device of FIG. 4E.
Figure 4G:
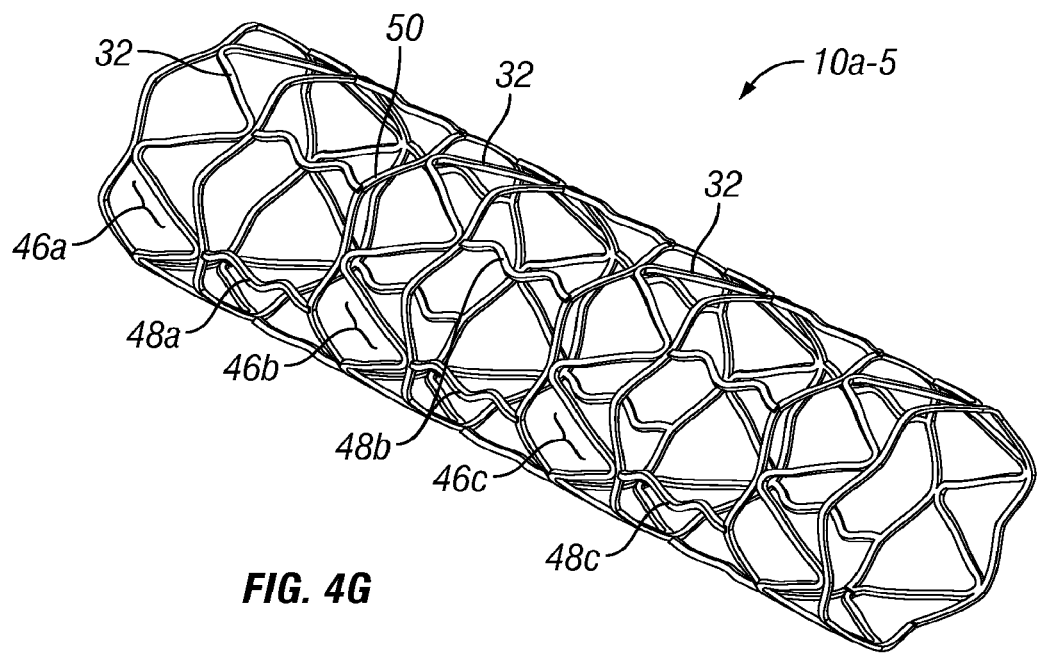
FIG. 4G is a perspective view of an endovascular device of the present invention having the general design shown in FIG. 4E in a fully assembled, first expanded state.

FIGS. 4E through 4G show another embodiment 10a-5 of an endovascular device of the present invention which comprises a plurality of self-expanding structures 46a, 46b, 46c, a plurality of plastically deformable constraining members 50 and a plurality of linking members 48a, 48b which extend between the self-expanding structures 46a, 46b, 46c. The self-expanding structures 46a, 46b, 46c of this embodiment 10a-5 can be of the same construction as the self-expanding structures 38 of above-described embodiment 10a-3. Also, the plastically deformable constraining members 50 of this embodiment 10a-5 can be of the same construction as the plastically-deformable constraining members 40 of above-described embodiment 10a-3. The linking members 48a, 48b are plastically deformable members (e.g., wires) having a series of curves formed therein. As may be appreciated from the enlarged view of FIG. 4F, opposite ends of each plastically deformable linking member 48a, 48b are connected to adjacent ones of the plastically-deformable constraining members 50, which are in-turn laced through the peeks of the zig-zag members 52 of which the self-expanding members 46a, 46b, 46c are comprised. These linking members 48a, 48b can be formed of any suitable plastically deformable material (e.g., metals, plastics). In this particular embodiment, each linking member 48a, 48b comprises a thin metal wire that has a series of sinusoidal waves formed therein. This embodiment 10a-5 is implanted in a tortuous or curved segment of vein and the width of the sinusoidal waves in each linking member 48a, 48b may elongate, compress or stay the same, thereby allowing this embodiment 10a-5 to be conformed or shaped in situ to match the particular tortuous or curved anatomy of the vein in which it is implanted.

Figure 4H:
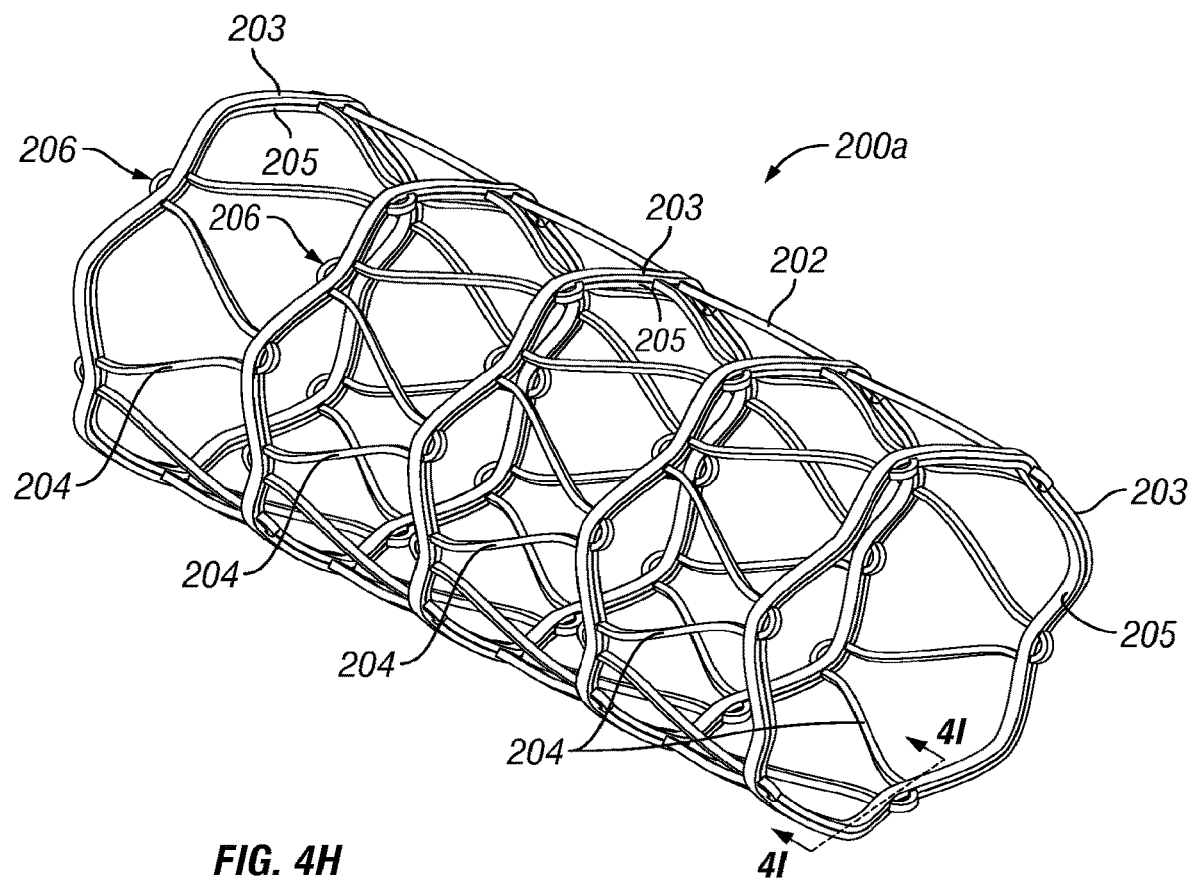
FIG. 4H shows another embodiment of an endovascular device of the present invention in a first expanded state.
Figure 4I:
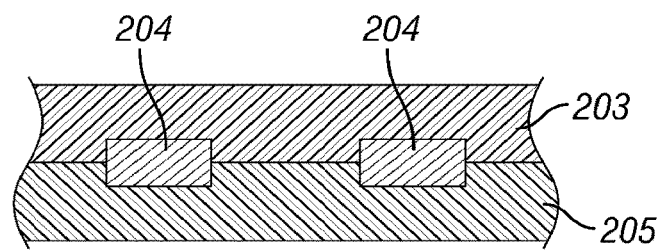
FIG. 4I is a cross sectional view through line 4I-4I of FIG. 4H.

FIGS. 4H and 4I show another embodiment of an endovascular device 200a of the present invention. FIG. 4H shows the device 200a in a first expanded state. This device 200a comprises outer polymer ring members 203, self expanding zig-zag ring members 204 having vertexes 206 and inner polymer rings 205. The outer polymer rings 203 are disposed around the outer surfaces of the vertexes 206 of neighboring zig-zag ring members 204 and the inner polymer rings 205 are disposed about the inner surfaces of the vertexes 206 of neighboring zig-zag ring members 204. The outer and inner polymer rings 203, 205 are then bonded to one another (e.g., by heat bonding or other suitable means) thereby capturing and interconnecting the vertexes 206 of neighboring zig-zag ring members 204. In this manner, the bonded outer and inner polymer rings 203, 205 limit the self expansion of the zig-zag ring members 204 to a first expanded state and also maintain the zig-zag ring members 204 in a unitary interconnected series. After the device 200a has been positioned within a desired vessel and allowed to self expand to the first expanded state, one or more expansion tool(s), such as balloon(s), may be advanced into the device 200a and used to further expand and deform one or more of the bonded outer and inner polymer rings 203, 205, thereby allowing some or all of the device 200a to further expand to a second expanded state. In this manner, the outwardly directed pressure exerted by the device 100a on the vessel wall may be customized or fine tuned at the time of implantation of the device. As in other embodiments of the present invention, this ability to undergo in situ adjustment of the expanded diameter or outward pressure exerted by all or certain region(s) of the device 200a, allows the operator to cause the device 200a to exert sufficient outward pressure on the wall of the vessel (e.g., vein) to maintain frictional engagement and prevent migration of the device while at the same time exerting outwardly directed pressure that is low enough to prevent unwanted embedding of the device in, or penetration through, the wall of the vessel (e.g., vein) in which it is implanted.

Figure 4J:
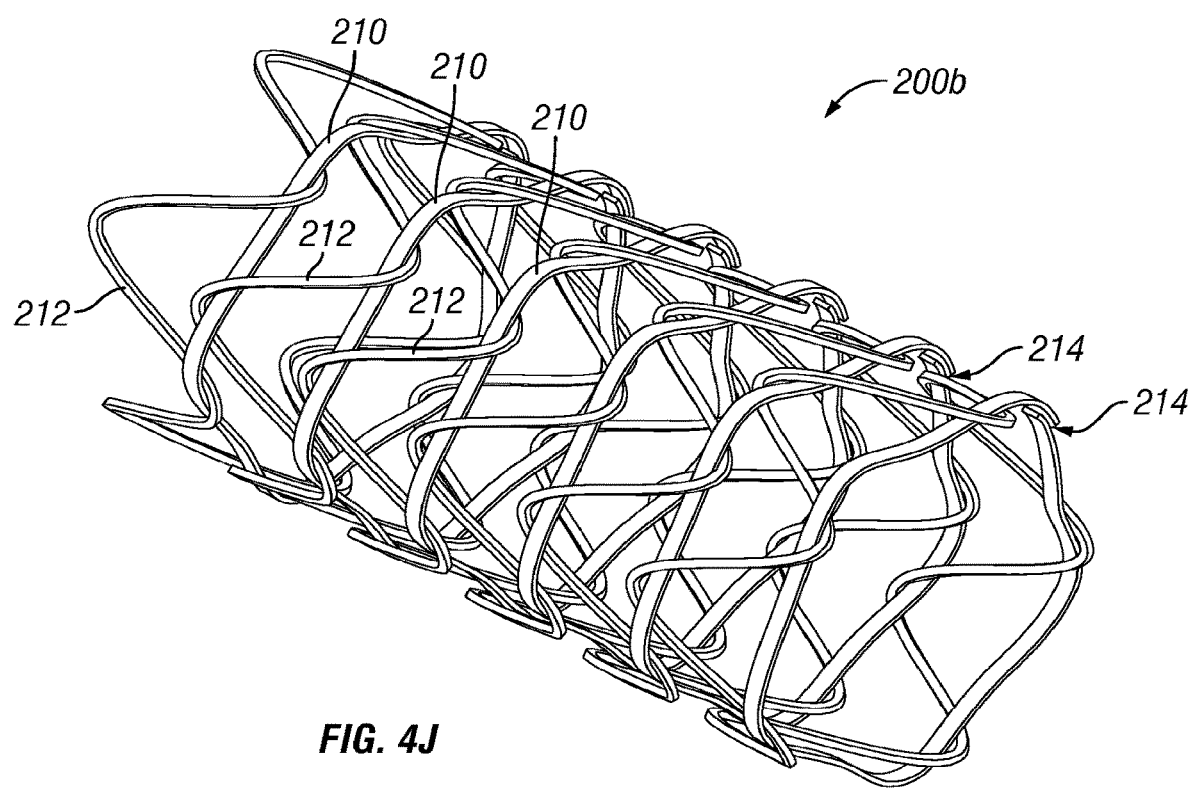
FIG. 4J shows another embodiment of an endovascular device of the present invention in a first expanded state.

FIG. 4J shows another device 200b of the present invention in a first expanded state. This device 200b comprises a series of zig-zag ring members 212 with polymer bands 210 laced through the vertexes of adjacent zig-zag ring members 212. The opposite ends of each polymer band 210 overlap, as shown, and are bonded (e.g., heat bonded) together to form a fused region 214 on each band 210. In this manner, the diameter of each polymer band 210 limits the self expansion of the zig-zag ring members 212 to a first expanded state and also the bands 210 interconnect the zig-zag ring members 212 in series. After the device 200b has been positioned within a desired vessel and allowed to self expand to the first expanded state, one or more expansion tool(s), such as balloon(s), may be advanced into the device 200b and used to further diametrically expand and deform one or more of the bands 210, thereby allowing some or all of the device 200b to further expand to a second expanded state. In this manner, the outwardly directed pressure exerted by the device 200b on the vessel wall may be customized or fine tuned at the time of implantation of the device. As in other embodiments of the present invention, this capability for in situ adjustment of the expanded diameter or outward pressure exerted by all or certain region(s) of the device 200b allows the operator to adjust the device 200b so that it exerts sufficient outward pressure on the wall of the vessel to maintain frictional engagement and prevent unwanted slippage or migration of the device while at the same time causing the outwardly directed pressure to remain low enough to prevent unwanted migration of the device into or through the wall of the vessel (e.g., vein) in which it is implanted.

Figure 4K:
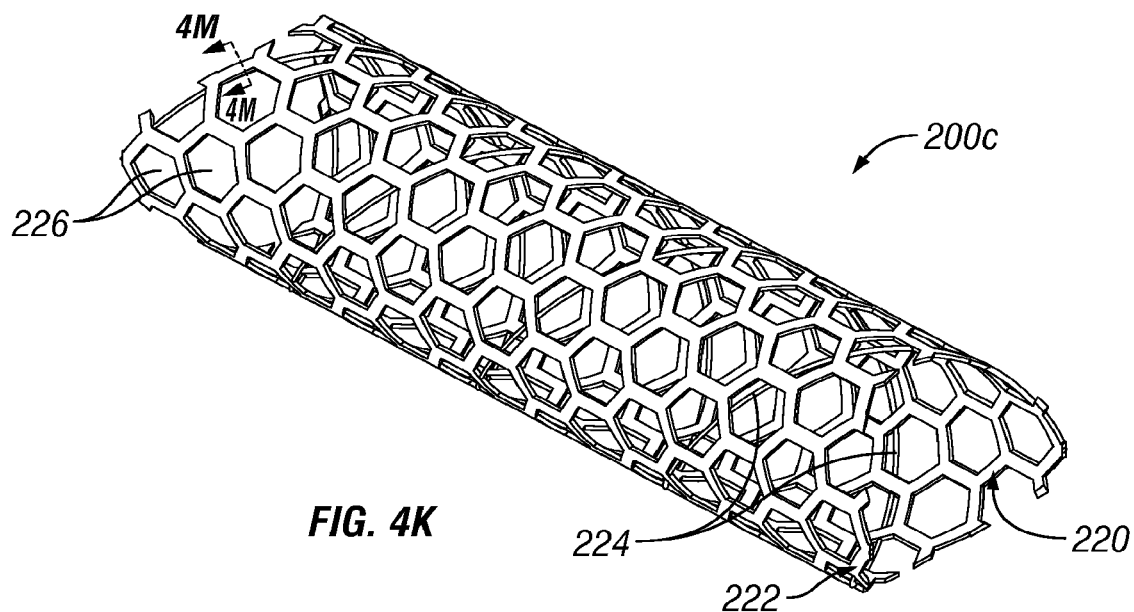
FIG. 4K shows another embodiment of an endovascular device of the present invention in a first expanded state.
Figure 4L:
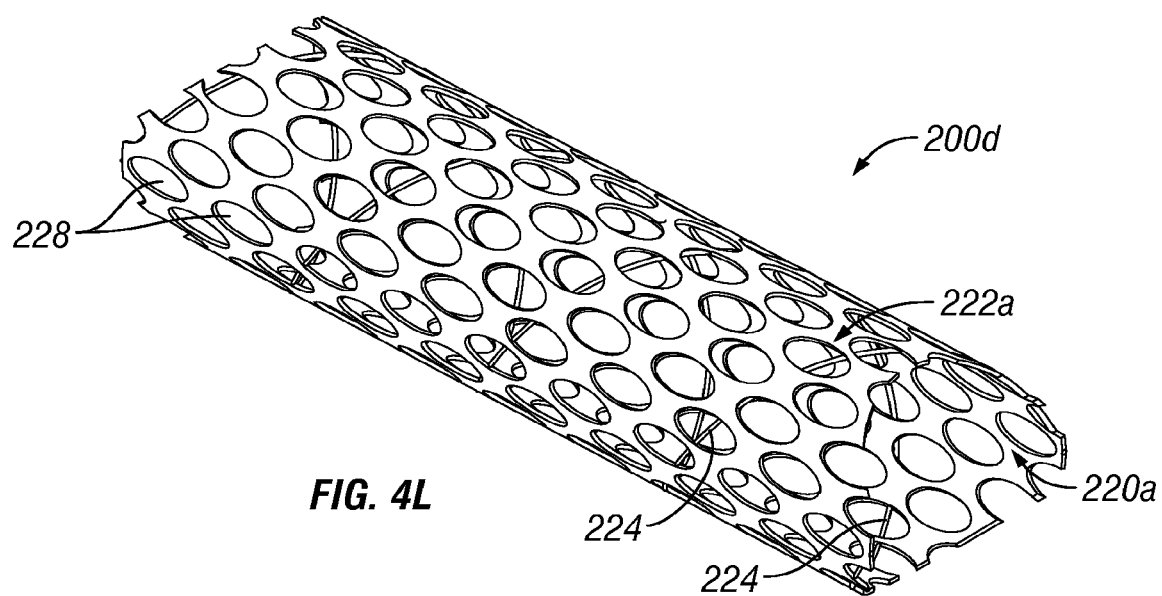
FIG. 4L shows another embodiment of an endovascular device of the present invention in a first expanded state.
Figure 4M:
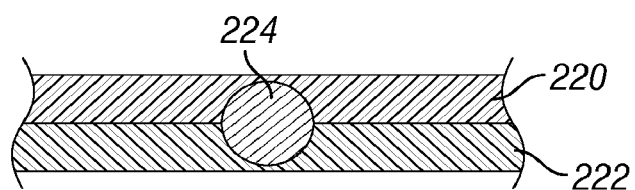
FIG. 4M is a cross sectional view through line 4M-4M of FIG. 4K.
Figure 5:
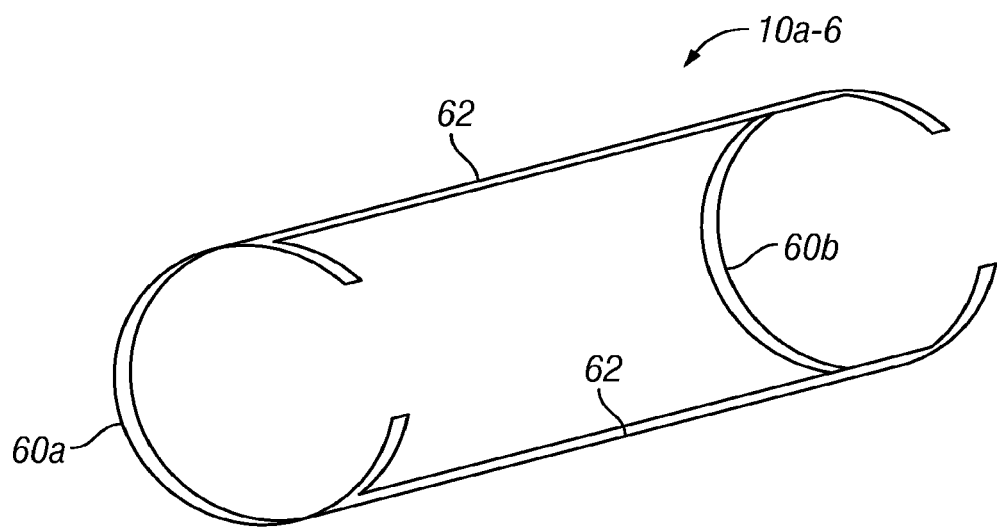
FIG. 5 shows another embodiment of an endovascular device of the present invention in an expanded state.
Figure 5A:
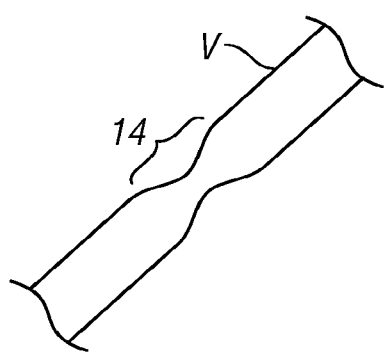
FIGS. 5A and 5B show steps in a method wherein the device of FIG. 5 is implanted in a stenotic vein to improve blood flow through the stenosis.
Figure 5B:
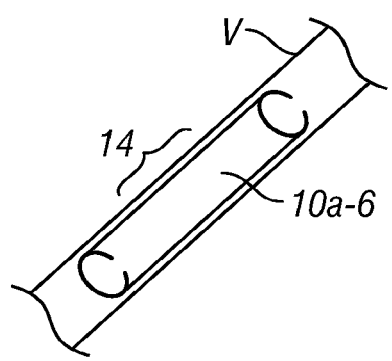

FIGS. 4K through 4M show other embodiments of devices 200c and 200d wherein a self-expanding member, such as a wire helix, in combination with one ore more perforated tubular sheets of material (e.g., perforated plastic film or sheet). In particular, the device 200c shown in FIGS. 4K and 4M comprises a self-expanding member 224 in the form of a wire helix captured between an inner polymer layer 220 and an outer polymer layer 222 which have been fused (heat fused) to one another in the manner shown in FIG. 4M and which have polygonal (e.g. hexagonal) perforations. The inner and outer polymer layers 220, 222 may be formed of any suitable deformable polymeric material, such as expanded polytetrafluoroethylene (ePTFE). FIGS. 5, 5A and 5B show yet another embodiment 10a-6 of an endovascular device of the present invention comprising full or partial ring members 60a, 60b with two or more strut members 62 extending therebetween. The full or partial ring members 60a, 60b can be self-expanding or pressure expandable and positioned within a vein V on either side of a stenotic region 14 so that the strut members 62 cause the stenotic region 14 to expand in at least one diametric plane. The strut members in one embodiment are leaf spring structures that provide an outward force against the vein but will not provide an outward force beyond their straightened configuration. Where more than two strut members 62 are used, such will cause expansion of the stenotic region 14 in more than one diametric plane. This embodiment 10a-6 can be formed of thin wire or other suitable thin material to minimize the amount of foreign material in blood contact within the subject's flowing blood and to minimize turbulence creation within the vein.

Figure 6:
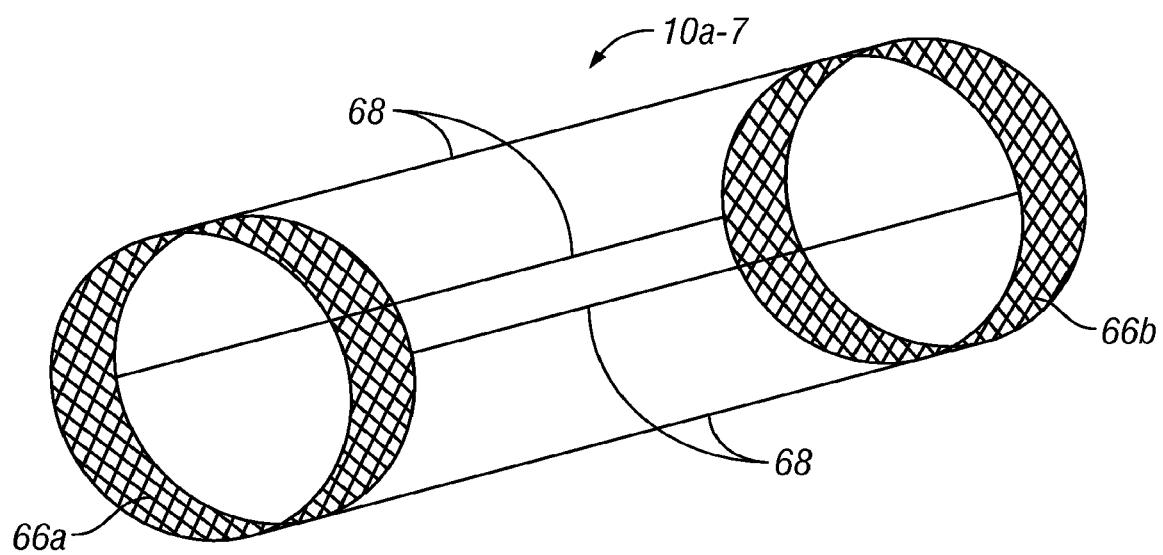
FIG. 6 shows another embodiment of an endovascular device of the present invention in an expanded state.
Figure 6A:
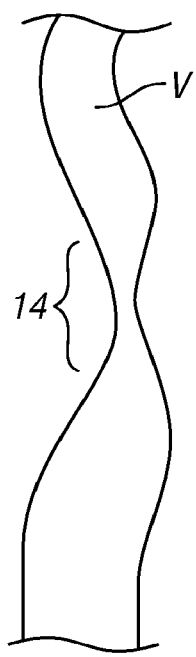
FIGS. 6A and 6B show steps in a method wherein the device of FIG. 6 is implanted in a stenotic vein to improve blood flow through the stenosis.
Figure 6B:
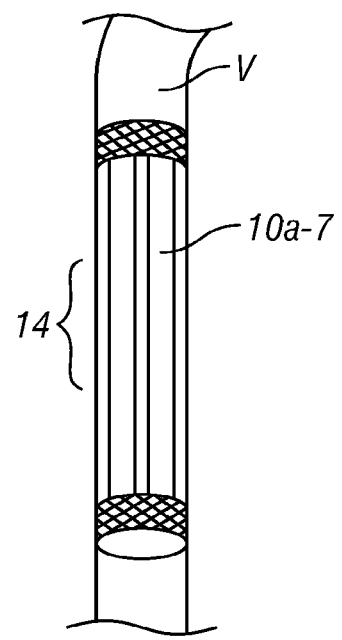

FIGS. 6, 6a and 6b show another embodiment 10a-7 of an endovascular device of the present invention which comprises radially expandable members 66a and 66b with a plurality of linear elements 68 traversing therebetween.

Figure 7A:
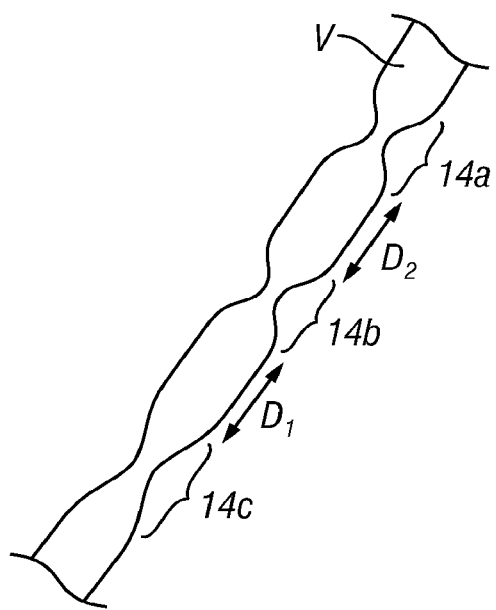
FIG. 7A shows a vein having several discrete stenotic regions.

In patients who suffer from CCVI, the number, topography and location(s) of venous stenoses may vary. For example, FIG. 7A shows a vein V having three discrete stenotic regions 14a, 14b and 14c at spaced apart locations, as may be determined by venography, MRI or other imaging techniques. Stenotic region 14c is substantially longer than stenotic regions 14a and 14b. The distances $D_1$, $D_2$ between the stenotic regions 14a, 14b, 14c can also differ. In view of this, in some embodiments of the devices of the present invention, the devices may be custom-configured or custom-expanded to match a number of stenoses of differing length and/or severity.

Figure 7B:
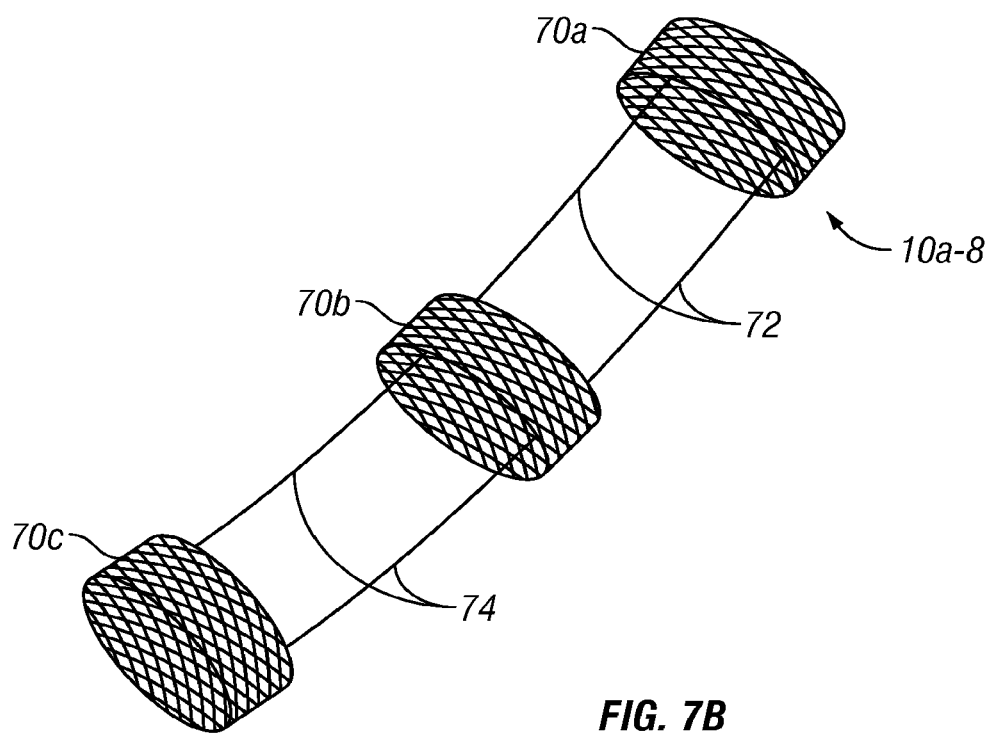
FIG. 7B shows another embodiment of an endovascular device of the present invention in an expanded state, such device having been custom-made for implantation in the vein of FIG. 7A.

For example, FIG. 7B shows a device 10a-8 which comprises radially expandable (i.e., self-expanding and/or pressure-expandable) scaffolding members 70a, 70b and 70c connected together by longitudinal members 72, 74. The scaffolding members 70a, 70b and 70c are specifically sized to correspond to the sizes of the stenotic regions 14a, 14b, 14c. The lengths of the longitudinal members 72, 74 correspond to the distances D1, D2 between the stenotic regions. Thus, this embodiment 10a-8 is advanced into the vein V while in a collapsed state and positioned such that scaffold member 70a is within stenotic region 14a, longitudinal members 72 extend through the segment of vein V between stenotic regions 14a and 14b, scaffold member 70b is within stenotic region 14b, longitudinal members 74 extend through the segment of vein V between stenotic regions 14b and 14c and scaffold member 70b is within stenotic region 14b. Thereafter, the scaffold members 70a, 70b and 70c are caused or allowed to radially expand so as to dilate the stenotic regions 14a, 14b, 14c while longitudinal members 72 and 74 extend through non-stenotic regions of the vein V. Those longitudinal members remain close to or in contact with the wall of the vein V, thereby minimizing obstruction to blood flow through those regions of the vein V and risk of thrombosis.

Figure 7C:
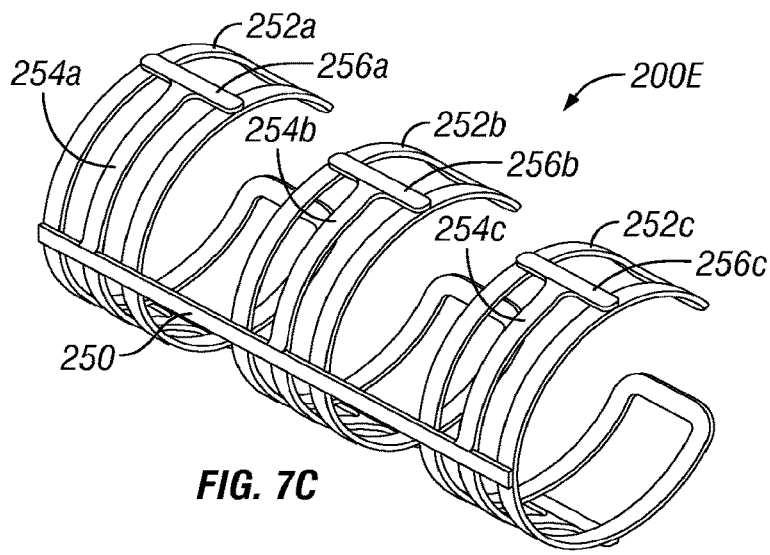
FIG. 7C shows another embodiment of an endovascular device of the present invention in a first expanded state.

FIG. 7C shows an endovascular device 200e comprising slotted self-expanding, C-shaped scaffold members 252a, 252b and 252c attached to at least one longitudinal member 250 and having plastically deformable C-shaped constraining members 254a, 254b, 254c which limit the degree to which each scaffold member 252a, 252b, 252c may self-expand. The slotted C-shaped scaffold members 252a, 252b and 252c are formed of elastic or superelastic material, such as Elgiloy or nickel-titanium, and are preset to a fully expanded configuration such that, when unconstrained, they will self-expand to that fully expanded configuration. In some embodiments, more than one longitudinal member 250 may be provided. The number, flexibility and configuration of the longitudinal member(s) 250 may vary depending on the configurational and flexibility requirements of the device 200E. The longitudinal member(s) 250 formed of any suitable polymer of other material, such as PTFE, ePTFE or polyurethane, or stainless steel or nickel-titanium. Plastically deformable C-shaped constraining members 254a, 254b, 254c are attached, in this example by way of cross members 256a, 256b, 256c, to each slotted C-shaped scaffold member 252a, 252b and 252c. These plastically deformable C-shaped constraining members 254a, 254b, 254c may be formed of any suitable deformable material, such as PTFE, ePTFE, polyurethane, stainless steel or nickel-titanium. After this device 200e has been delivered into the lumen of a stenotic vein it is relieved of constraint and allowed to self expand to a first expanded configuration which is smaller in diameter than the fully expanded configuration to which the scaffold members 252a, 252b and 252c are capable of expanding. This first expanded configuration is limited by the pre-set shapes of the plastically deformable constraining members 254a, 254b, 254c. Thereafter, one or more balloon(s) or other expandable members positioned within the slotted C-shaped scaffold members 252a, 252b and 252c is/are used to further expand each scaffold member 252a, 252b and 252c to a desired second diameter by deforming each plastically deformable expansion limiter 254a, 254b, 254c. In this manner, some or all of the scaffold members 252a, 252b and 252c may be expanded to different diameters to accommodate regional variations in the presence or severity of vessel narrowing.

Figure 7D:
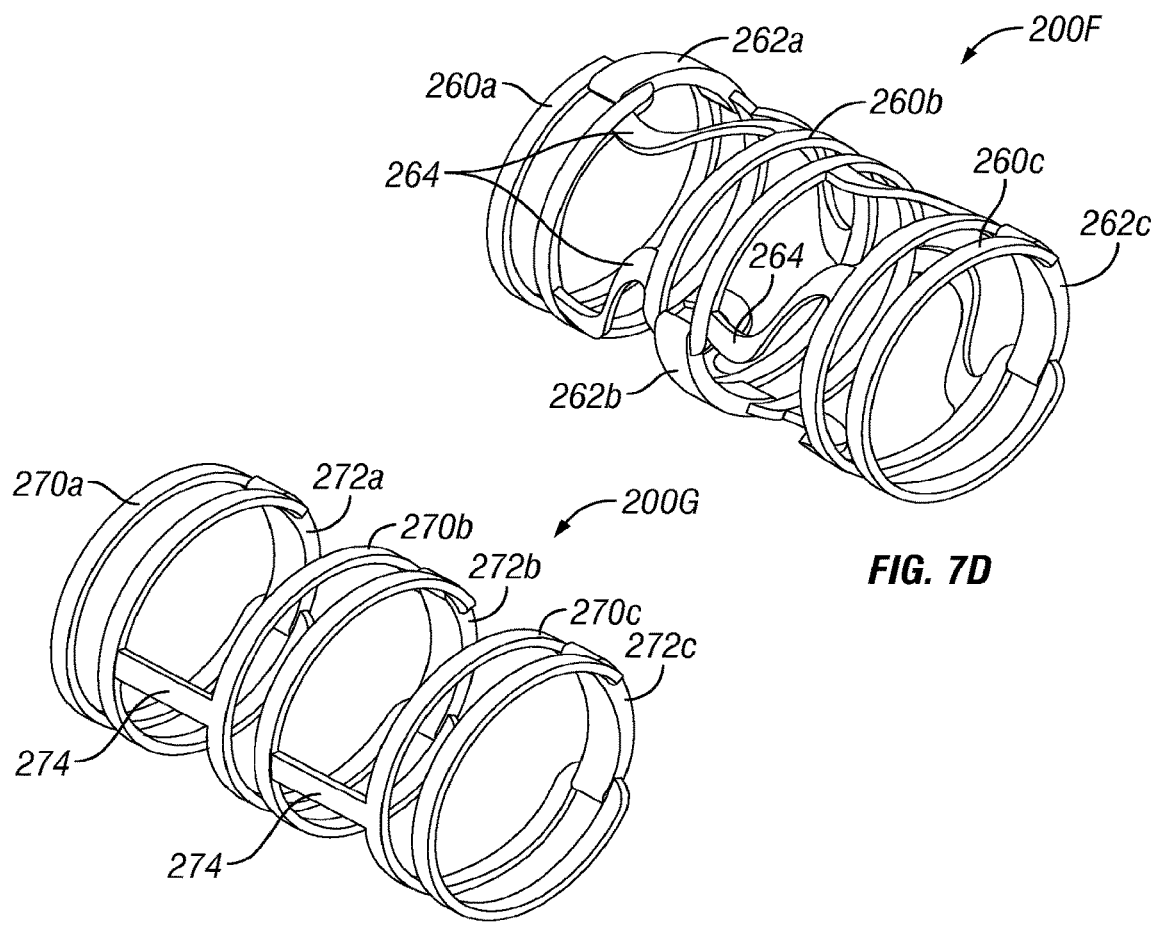
FIG. 7D shows another embodiment of an endovascular device of the present invention in a first expanded state.

The device 200f shown in FIG. 7D also comprises a series of slotted, self-expanding, C-shaped scaffold members 260a, 260b and 260c. However, in this embodiment, the device 200f has a plurality of separate curved linking members 264 which interconnect the scaffold members 260a, 260b and 260c and provide for additional flexibility of the device 200F as compared to devices having a continuous longitudinal member 250 as seen in FIG. 7C. Also, in this device 200f, the initial expansion of each scaffold member 260a, 260b and 260c is limited by a longitudinally extendable constraining linker 262a, 262b, 262c which connects the opposing ends of each C-shaped scaffold member 260a, 260b, 260c. The materials used in the manufacture of the components of this device 200f may be the same as those described above with respect to the device 200e of FIG. 7E. In operation, this device 200f may be delivered into the lumen of a stenotic vein and relieved of constraint so that it self-expands to a first expanded configuration which is smaller in diameter than the fully expanded configuration to which the scaffold members 260a, 260b and 260c are capable of expanding. This first expanded configuration is limited by the pre-set lengths of the constraining linkers 262a, 262b, 262c. Thereafter, one or more balloon(s) or other expandable members positioned within the slotted C-shaped scaffold members 260a, 260b and 260c is/are used to further expand each scaffold member 260a, 260b and 260c to a desired second diameter by causing the constraining linkers 262a, 262b, 262c to lengthen. In this manner, some or all of the scaffold members 260a, 260b and 260c may be expanded to different diameters to accommodate regional variations in the presence or severity of vessel narrowing.

Figure 7E:
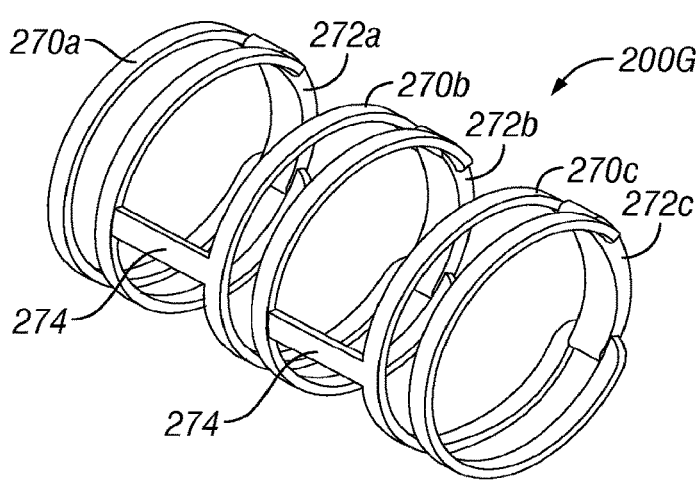
FIG. 7E shows another embodiment of an endovascular device of the present invention in a first expanded state.

FIG. 7E shows a device 200g which comprises a series of slotted, self-expanding, C-shaped scaffold members 270a, 270b and 270c and longitudinally extendable constraining linker 272a, 272b, 272c the same as those described above with respect to the device 200f of FIG. 7D. However, this device 200g differs from the device 200f of FIG. 7D in that it has straight linking members 274 rather than the curved linking members 264. The device 200g would be more advantageous when longitudinal stiffness is needed. Device 200f would be more advantageous when longitudinal flexibility is needed such as in curved lumens.

Figure 7F:
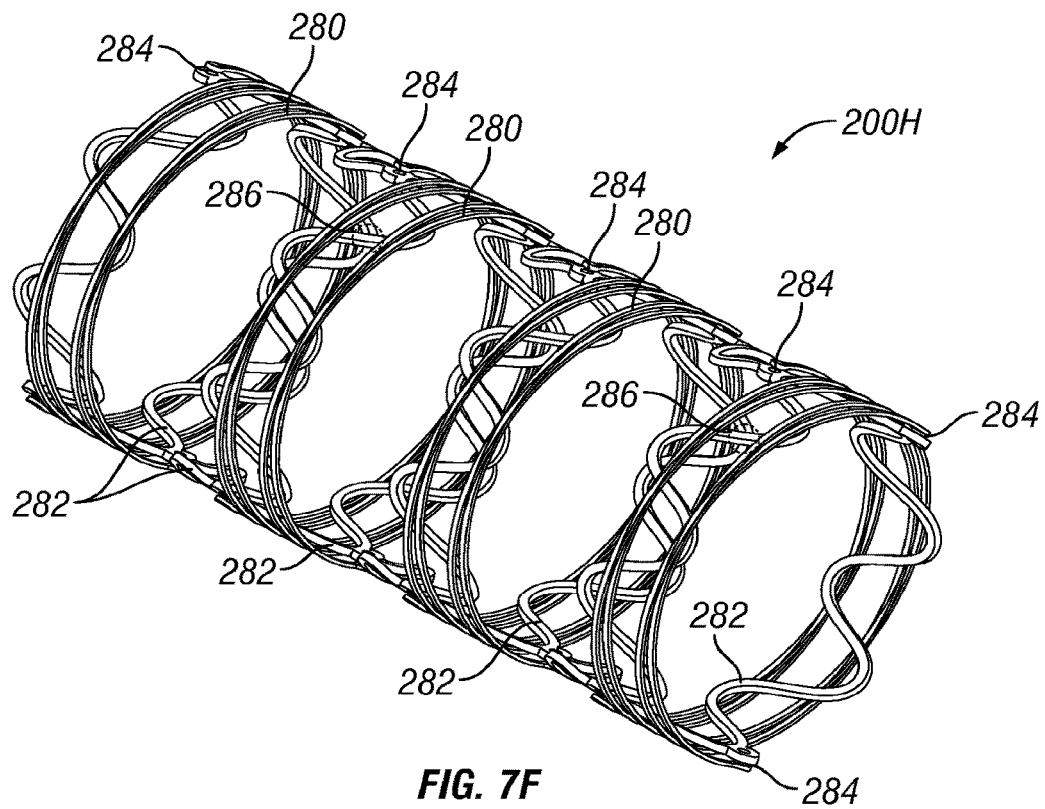
FIG. 7F shows another embodiment of an endovascular device of the present invention in a first expanded state.

FIG. 7F shows a device 200h which comprises a series of self-expanding scaffold members 282 in the form of zig-zag rings with deformable restriction bands 280 wrapped therearound. The restriction bands 280 are fixed to a series of small holes 284 on each scaffold member 282. At locations 286 where the restriction bands 280 cross one another, they may be fused, adhered or sintered together or they may remain free. In this example, the restriction bands 284 are shown only on the outside of the scaffold members 282 but alternatively may be disposed on the inside of, or may be woven inside and outside of, the scaffold members 282. The scaffold members 282 may be formed of any suitable self-expanding material as described above. For example, they may be laser cut from a tube formed of superelastic metal such as nickel-titanium alloy. The restriction bands 280 may be formed of any suitable deformable material such as ePTFE or polyurethane. The restriction bands 280 are initially sized to limit the self-expansion of the scaffold members 282 to a first expanded configuration which is smaller in diameter than the fully expanded configuration to which the scaffold members 260a, 260b and 260c are capable of expanding. In operation, this device 200f may be delivered into the lumen of a stenotic vein and relieved of constraint so that it self-expands to a first expanded configuration which is smaller in diameter than the fully expanded configuration to which the scaffold members 260a, 260b and 260c are capable of expanding. This first expanded configuration is limited by the pre-set lengths of the constraining linkers 262a, 262b, 262c. Thereafter, one or more balloon(s) or other expandable members positioned within the slotted C-shaped scaffold members 260a, 260b and 260c is/are used to further expand each scaffold member 260a, 260b and 260c to a desired second diameter by causing the constraining linkers 262a, 262b, 262c to lengthen. In this manner, some or all of the scaffold members 260a, 260b and 260c may be expanded to different diameters to accommodate regional variations in the presence or severity of vessel narrowing.

Figure 7G:
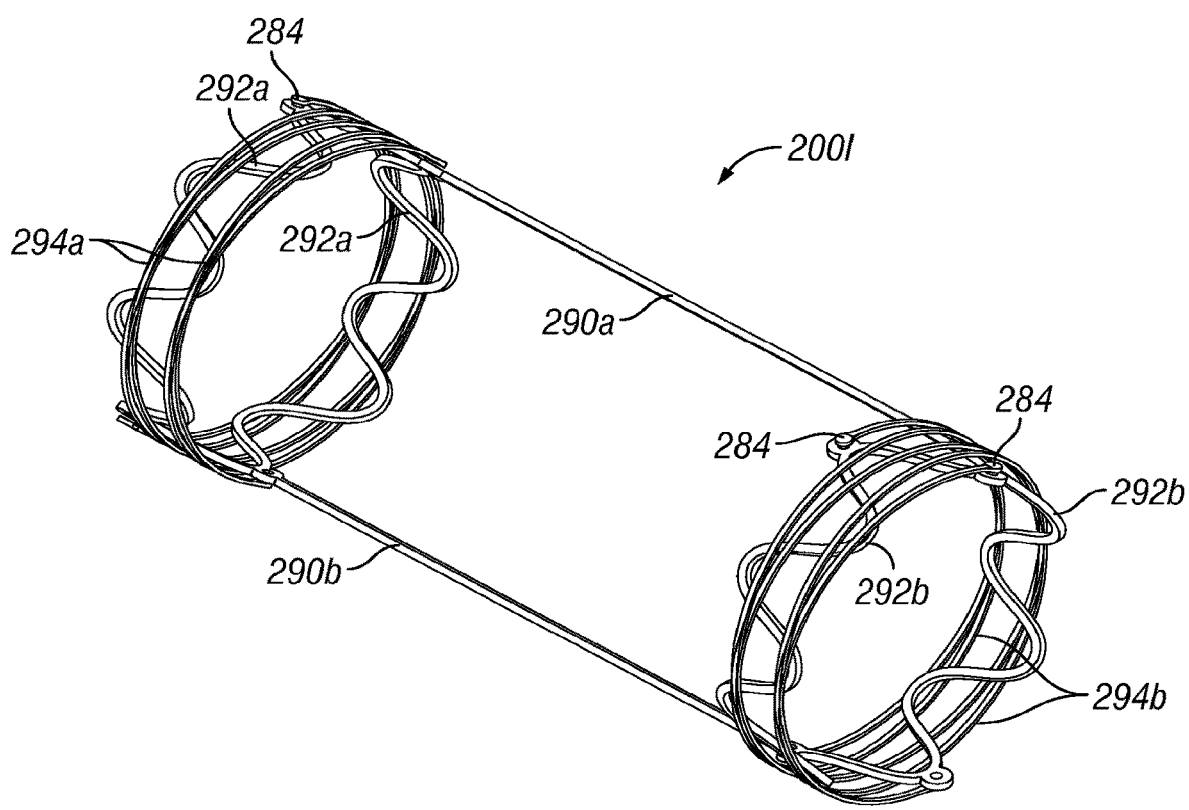
FIG. 7G shows another embodiment of an endovascular device of the present invention in a first expanded state.

FIG. 7G shows a device 200I that comprises a first and second zig-zag rings 292a, 292b that are connected to one another by way of longitudinal members 290a, 290b and which have polymer restriction bands 294a, 294b wrapped therearound and affixed to small holes 284 in the same manner as described above with respect to FIG. 7F. However, this device 200I differs from the device 200H of FIG. 7F in that it has only two zig-zag rings 292a, 292b and the area between them is occupied only by the longitudinal members 290a, 290b which, when implanted, will be in contact with the blood vessel and substantially parallel to blood flow, thereby causing minimal disruption of blood flow between the zig-zag rings 292a, 292b. Of course this example is non-limiting and varying numbers of zig-zag rings and longitudinal members may be used.

Figure 8:
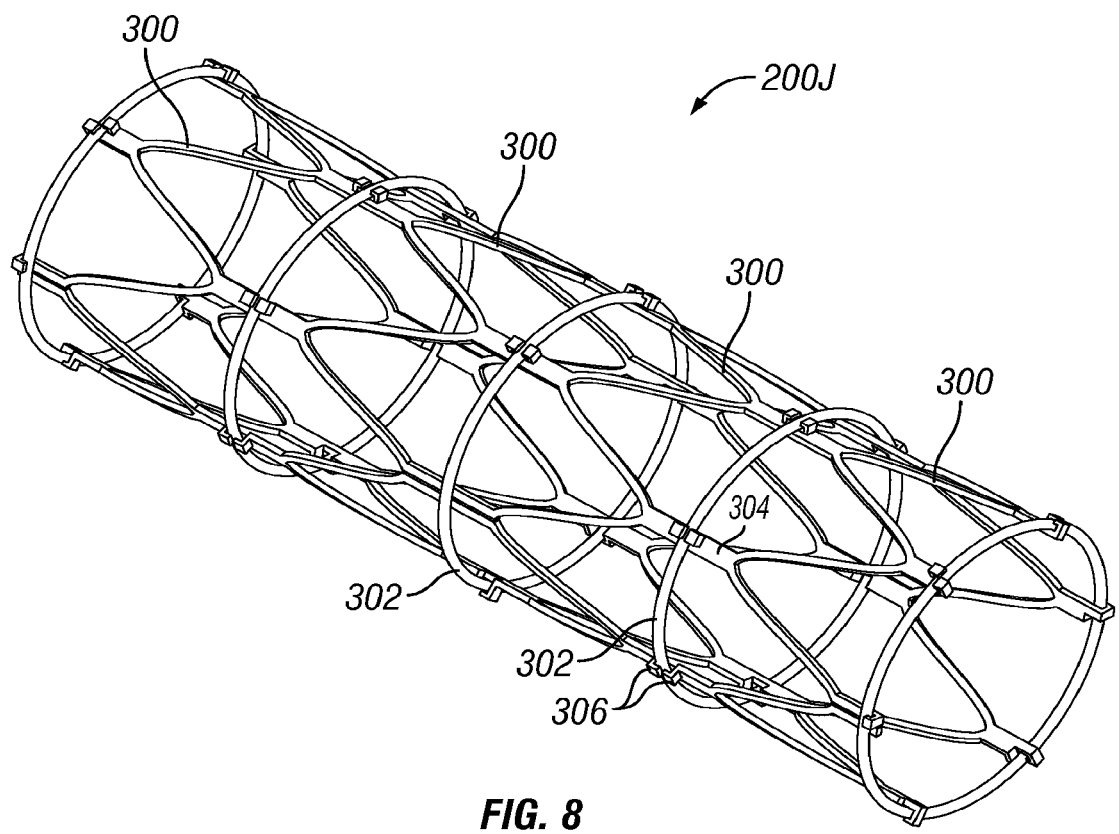
FIG. 8 shows another embodiment of an endovascular device of the present invention in a first expanded state.
Figure 8A:
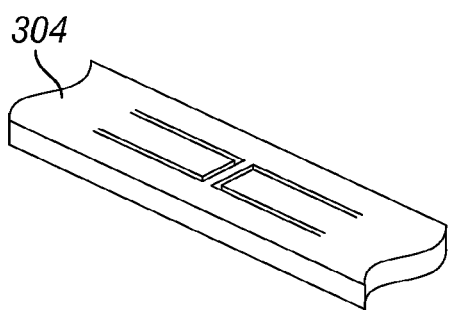
FIG. 8A shows a cut-away view of a portion of the device of FIG. 8 whereon regions have been cut away to permit the formation of guide protrusions.
Figure 8B:
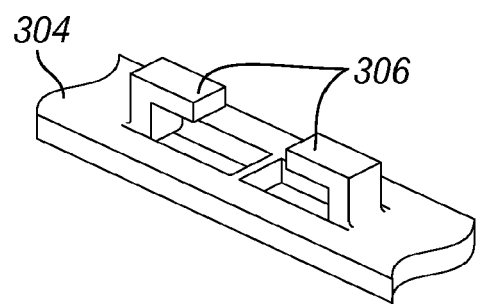
FIG. 8B shows the same portion of the device as illustrated in FIG. 8A after the cut away regions have been deformed to create desired guide protrusions.

FIGS. 8 through 8B show yet another endovascular device 200J useable for stenting veins or other body lumens. This device 200J comprises an elongate self-expanding stent which comprises a series of zig-zag rings 300 linked together by longitudinal linking members 304. Deformable restriction bands 302 extend around the longitudinal linking members, as shown. Alternatively or additionally, the restriction bands 302 may extend around the zig-zag rings 300. The polymer restriction bands 302 may be affixed to or held in place on the longitudinal linking members 304 and/or zig-zag rings 300 by any suitable means, such as by heat fusing the bands to the longitudinal linking members, by adhesive or by crimp connection. In the particular example shown, tabs 306 are cut in the longitudinal members 304 and crimped in the manner shown in FIGS. 8A and 8B to thereby hold the restriction bands 302 in place at the midpoint of each longitudinal member 304 by crimp connection. The zig-zag rings 300 and longitudinal members 304 may be formed of any suitable self-expanding material as described above. For example, they may be laser cut from a tube formed of superelastic metal such as nickel-titanium alloy. The restriction bands may be formed of any suitable deformable material such as ePTFE or polyurethane. The restriction bands 302 are initially sized to limit the self-expansion of the zig-zag rings 300 to a first expanded configuration which is smaller in diameter than the fully expanded configuration to which the zig-zag rings 300 are capable of expanding. In operation, this device 200I may be delivered into the lumen of a stenotic vein and relieved of constraint so that it self-expands to a first expanded configuration which is smaller in diameter than the fully expanded configuration to which the zig-zag rings 300 are capable of expanding. This first expanded configuration is limited by the pre-set lengths of the restriction bands. Thereafter, one or more balloon(s) or other expandable members positioned within the zig-zag rings 300 is/are used to further expand each zig-zag ring 300 to a desired second diameter by causing the restriction bands 302 to lengthen. In this manner, some or all of the zig-zag rings 300 may be expanded to different diameters to accommodate regional variations in the presence or severity of vessel narrowing.

Figure 9A:
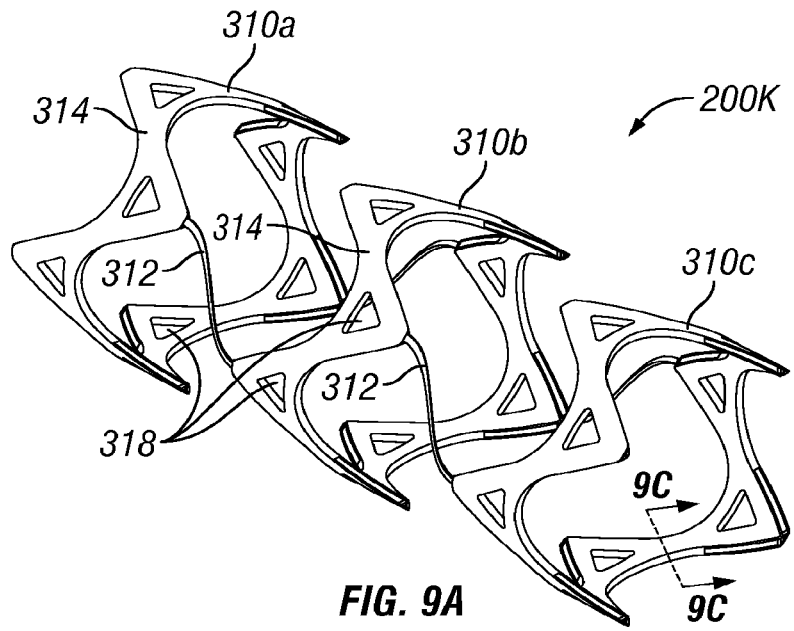
FIG. 9A shows another embodiment of an endovascular device of the present invention in a first expanded state.
Figure 9B:
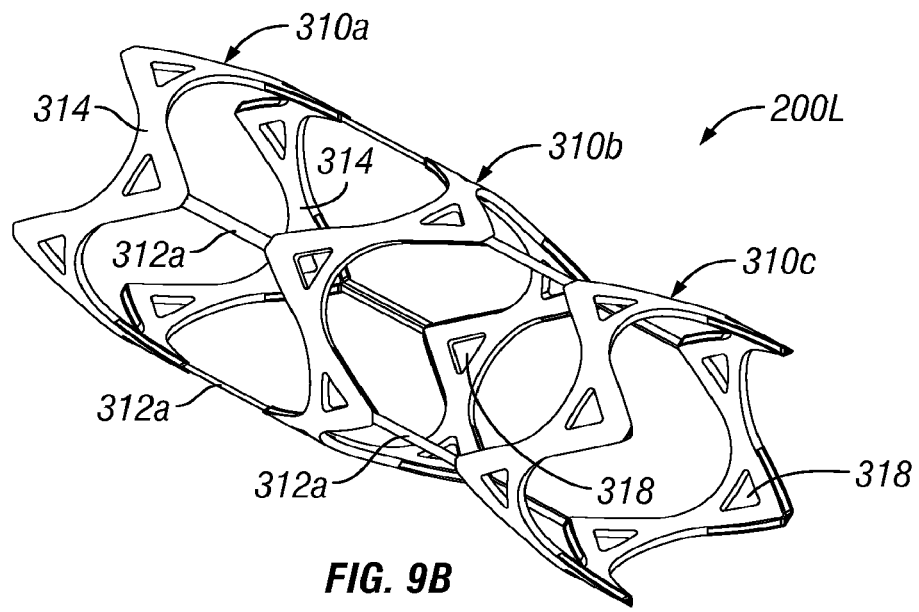
FIG. 9B shows another embodiment of an endovascular device of the present invention in a first expanded state.
Figure 9C:
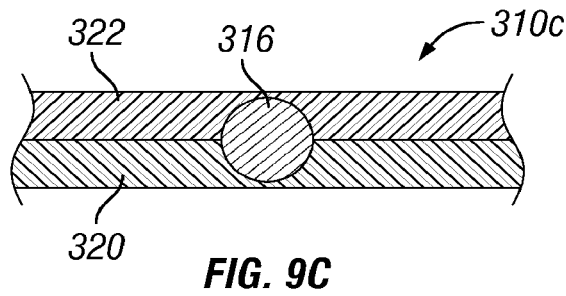
FIG. 9C is a cross sectional view through line 9C-9C of FIG. 9A.

FIGS. 9A and 9C show a device 200K which comprises plurality of self expanding, polymer covered scaffold rings 310a, 310b, 310c joined in series by curved linking members 312. Each polymer covered scaffold ring 310a, 310b, 310c comprises a self expanding metal ring 316 (such as a zig-zag or woven ring) covered with an expansion-restricting polymeric covering. One way in which to manufacture this device is to place the metal rings 316 on a mandrel between an outer polymer tube 322 and an inner polymer tube 320 and then heat fuse the polymer tubes to each other, as shown in the cross sectional view of FIG. 9C. Thereafter, portions of the fused polymeric material may be cut away and, optionally, perforations 318 may be formed in the polymeric material, thereby producing a desired configuration and density as seen in FIG. 9A. The expansion-restricting polymeric covering is initially sized to limit the self-expansion of the metal rings 316 to a first expanded configuration which is smaller in diameter than the fully expanded configuration to which the metal rings 316 are capable of expanding. The metal rings 316 may be formed of any suitable self-expanding material as described above. For example, they may be laser cut from a tube formed of superelastic metal such as nickel-titanium alloy. The polymer tubes 320, 322 may be formed of any suitable deformable material such as ePTFE or polyurethane. In operation, this device 200K may be delivered into the lumen of a stenotic vein and relieved of constraint so that it self-expands to a first expanded configuration which is smaller in diameter than the fully expanded configuration to which the metal rings 316 are capable of expanding. This first expanded configuration is limited by the pre-set size of the expansion-restricting polymer cover. Thereafter, one or more balloon(s) or other expandable members are positioned concurrently or separately within each scaffold ring 310a, 310b, 310c and used to further expand each scaffold rings 310a, 310b, 310c to a desired second diameter by causing the expansion-restricting polymer cover to deform to a larger diameter. In this manner, some or all of the scaffold rings 310a, 310b, 310c may be expanded to different diameters to accommodate regional variations in the presence or severity of vessel narrowing. In the example shown, the linking members 312 are formed of polymer covered metal.

FIG. 9B shows a device 200K that comprises the same polymer covered scaffold rings 310a, 310b, 310c as the device 200K of FIG. 9A but which has straight longitudinal linking members 312a instead of curved linking members 312 connecting the scaffold rings 310a, 310b, 310c to each other. The embodiment of FIG. 9B may be used instead of the embodiment of FIG. 9A in cases where additional longitudinal stiffness is needed. FIGS. 10A through 10I show a generic example of a method by which separate regions of any of the above-described endovascular devices may be expanded to differing diameters such that those different regions of the device will exert different outward forces on the adjacent areas of the vessel wall, thereby allowing the device to be customized to address regionalized variations in the presence of severity of the stenosis. Although the above-described devices have broad applicability for use in a variety of anatomical or synthetic graft lumens, they provide a number of unique advantages when implanted in veins, such as when used to treat venous stenoses of the type that occur in CCVI. These advantages include but are not necessarily limited to 1) the ability to be customized to match the specific between and/or the size/severity of the stenoses to be treated, 2) the ability to maintain dilation of stenotic area(s) of the vein while minimizing force exerted on the vein wall by the implanted device to avoid erosion through or perforation of the vein wall, 3) the ability to expand and contract to accommodate normal variations of vein diameter (e.g., periods of venodilation or application of transverse compressive force on the vein. FIGS. 10A through 10I illustrate at least some of these advantages.

Figure 10A:
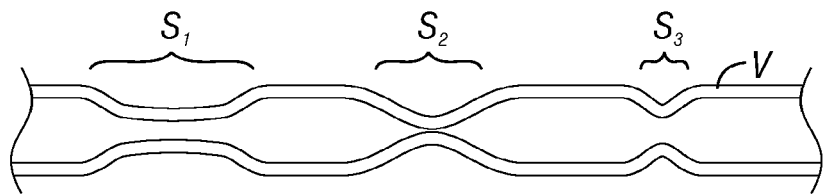
FIG. 10A is longitudinal sectional view of a vein having first, second and third stenotic regions of differing size and severity.

FIG. 10A shows a vein V having first $S_1$, second $S_2$ and third $S_3$ stenotic regions which differ in length and severity.

Figure 10B:
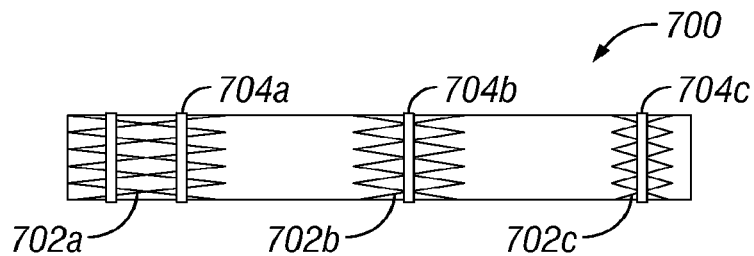
FIG. 10B is a side view of a self-expanding endovascular device of the present invention having first, second and third scaffold members sized and spaced for placement in the first, second and third stenotic regions of the vein of FIG. 10A.

FIG. 10B is a side view of a self-expanding endovascular device 700 of the present invention which has been custom made to match the stenotic regions $S_1$, $S_2$, $S_3$ of the vein V. This device 700 generally comprises first, second and third scaffold members 702a, 702b, 702c which are sized and spaced to match the first, second and third stenotic regions $S_1$, $S_2$, $S_3$. Each scaffold member 702a, 702b, 702c is formed of resilient material that is set to radially self-expand, when unconstrained and at normal body temperature, to a fully-expanded diameter that is generally greater than the diameter of the non-stenotic areas of the vein V. However, deformable expansion-limiting members 704a, 704b, 704c are provided to initially prevent the scaffold members 702a, 702b, 702c from self-expanding beyond a first diameter that is smaller that the fully-expanded diameter. This device 700 is shown in relatively generic fashion and may comprise any of the devices shown in FIGS. 3 through 9 as described above as well as various other possible embodiments not specifically shown or described in this patent application.

Figure 10C:
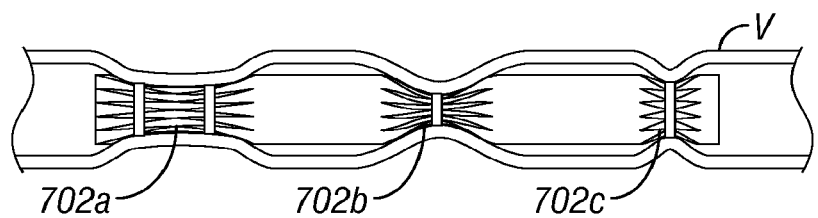
FIGS. 10C through 10G show steps in a method for implantation of the device of FIG. 10B in the vein of FIG. 10A.

FIGS. 10C through 10G show steps in a method for implanting the device 700 of FIG. 10B in the vein V of FIG. 10A. Initially, the device 700 is mounted on a delivery catheter (not shown) and held thereon in a collapsed configuration by a sheath, clips or other suitable catheter-based constraining means as well known in the art of delivering self-expanding stents. That delivery catheter, with the collapsed device 700 mounted thereon, is advanced into the vein V and the device 700 is positioned such that the first scaffold 702a is within the first stenotic region $S_1$, the second scaffold 702b is within the second stenotic region $S_2$ and the third scaffold 702c is within the third stenotic region $S_3$. Thereafter, with the device 700 so positioned, the sheath, clips or other suitable catheter-based constraining means is/are removed, allowing the device 700 to self-expand to the first expanded configuration, as seen in FIG. 10C. The delivery catheter is then removed. The outward force exerted by each scaffold member 702a, 702b, 702c at this stage of the procedure is insufficient to fully dilate the stenotic regions but, also, is desirably insufficient to cause erosion through or perforation of the vein V.

Figure 10D:
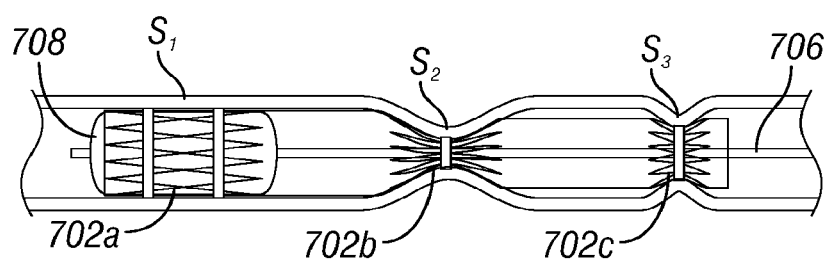

As seen in FIG. 10D, a balloon catheter 706 is then advanced into the vein V and its balloon 708 is positioned within the first scaffold 702a and first stenotic region $S_1$. The balloon 708 is then inflated sufficiently to cause therapeutic dilation (e.g., balloon angioplasty) of the first stenotic region $S_1$ while also deforming the first expansion-limiting members 704a to allow the first scaffold 702a to further self-expand to a second diameter. This second diameter is large enough to allow the scaffold 702a to coapts firmly with the inner surface of the vein wall, even when the vein V is in its most dilated state, but still does not exert so much pressure on the vein wall that it causes undesired erosion or perforation of the vein V. Thereafter, the balloon 708 is deflated and the catheter 706 is repositioned to cause the balloon 708 to be within the second scaffold 702b and second stenotic region $S_2$.

Figure 10E:
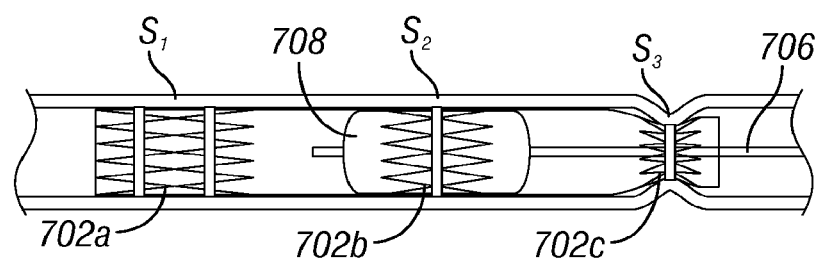

Thereafter, as seen in FIG. 10E, the balloon 708 is then inflated sufficiently to cause therapeutic dilation (e.g., balloon angioplasty) of the second stenotic region $S_2$ while also deforming the second expansion-limiting member 704b to allow the second scaffold 702b to further self-expand to a second diameter. That second diameter is sufficient to cause the second scaffold 702b to coapts firmly with the inner surface of the vein wall, even when the vein V is in its most dilated state, but still does not exert so much pressure on the vein wall that it causes undesired erosion or perforation of the vein V. Thereafter, the balloon 708 is again deflated and the catheter 706 is repositioned to cause the balloon 708 to be within the third scaffold 702c and third stenotic region $S_3$.

Figure 10F:
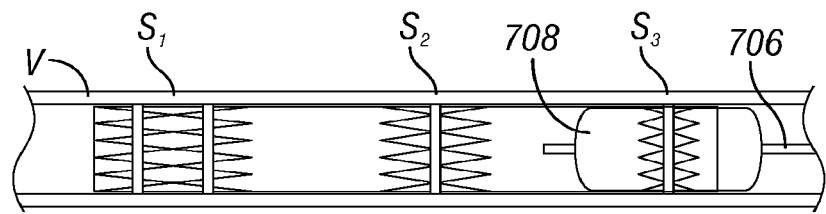

Thereafter, as seen in FIG. 10F, the balloon 708 is then inflated sufficiently to cause therapeutic dilation (e.g., balloon angioplasty) of the third stenotic region $S_3$ while also deforming the second expansion-limiting member 704b to allow the second scaffold 702b to further self-expand to a second diameter whereby it coapts firmly with the inner surface of the vein wall, even when the vein V is in its most dilated state, but still does not exert so much pressure on the vein wall that it causes undesired erosion or perforation of the vein V. Thereafter, the balloon 708 is again deflated and the catheter 706 is removed.

Figure 10G:
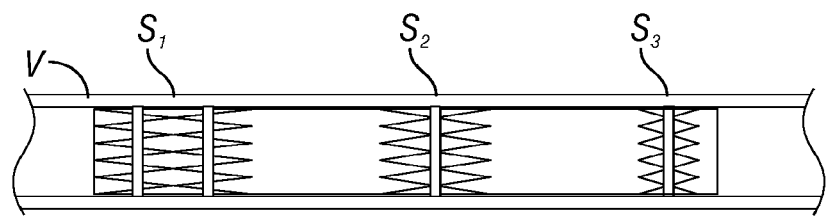

As seen in FIG. 10G, the balloon dilation has resulted in therapeutic dilation of all three stenotic regions $S_1$, $S_2$, $S_3$. The scaffold members 702a, 702b, 702c exert sufficient outwardly-directed force on the vein wall to maintain patency of, and to deter re-stenosis of, the stenotic regions $S_1$, $S_2$, $S_3$. However, the amount of force exerted by the scaffold members 702a, 702b, 702c and the diameter-limiting effect of the expansion-limiting members 704a, 704b, 704c serve to prevent the scaffold members 702a, 702b, 702c from eroding through or perforating the vein wall as has been reported to occur with other venous stents. In at least some embodiments, the scaffold members 702a, 702b, 702c may be constructed to exert a force in the range of from about 1 atm to about 8 atm on the vein wall, which is sufficient to maintain patency and deter migration of the device but not so forceful as to cause erosion or perforation of the vein wall.

Figure 10H:
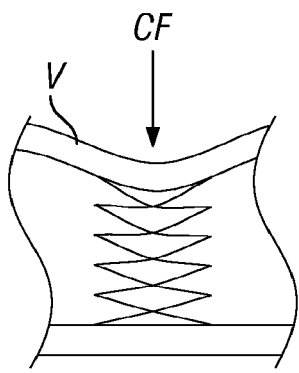
FIG. 10H is a schematic diagram showing the manner in which a self-expanding endovascular device of the present invention responds to the application of a transverse compressive force on the vein in which the device is implanted.
Figure 10I:
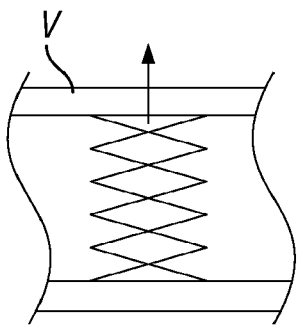
FIG. 10I is a schematic diagram showing the manner in which the device of FIG. 10H returns to its desired expanded configuration when the compressive force is removed.

FIG. 10H illustrates schematically the manner in which the self-expanding device 700 will radially compress in the event that some compressive force CF is applied to the vein. FIG. 10I shows how the device 700 springs back to its second diameter after the compressive force CF has been removed. This ability to withstand compressive forces without deformation of the device in important in applications where the device is implanted in a vein or other vessel that is near a body surface that is subject to occasional outside forces or other compression due to adjacent muscle contractions or skeletal movements.

Although the above-described examples relate to endovascular devices, the same customization method and regionalized variation in force exerted can also be used in connection with the exovascular devices of the present invention, including the various examples of exovascular devices described in the following paragraphs.

Figure 11:
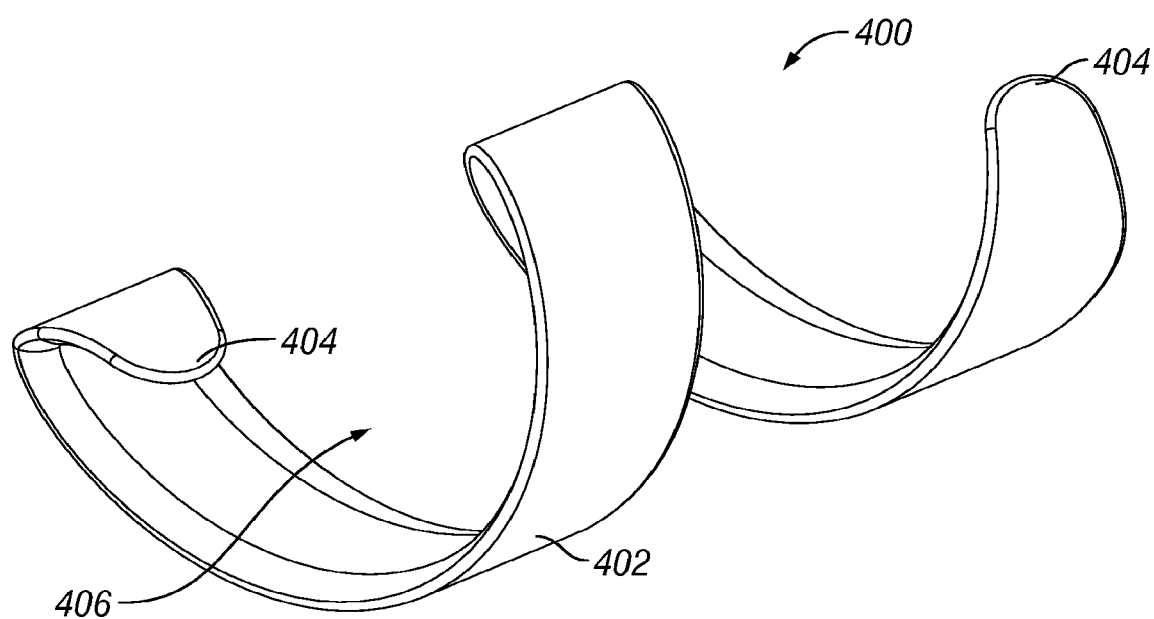
FIG. 11 shows another embodiment of an endovascular device of the present invention in a first expanded state.

FIG. 11 shows an exovascular support device 400 comprising a helically shaped strip of material 402 having a hollow channel 406 extending therethrough and blunt ends 404. This helically shaped strip 402 may be formed of any suitable materials such as polymers selected from polyurethanes or metals such as stainless steel or nickel-titanium. This device 400 may be surgically place around a blood vessel so that the blood vessel extends through the channel 406. In this manner the device 400 will prevent the blood vessel from being collapsed by transverse compressive forces that may be exerted on the blood vessel by external events (e.g., sleeping or resting against a surface that compresses one side of the neck) or anatomical/postural movements (e.g., lying down, turning the head, etc.). When used to treat CCVI, this device 400 could be implanted around a segment of a vein that drains blood from the brain (e.g., an internal jugular or azyogus vein) to prevent that segment of vein from becoming compressed when adjacent muscles are flexed or when any compressive force if applied. In some embodiments, the device 400 could also be adhered, sutured or otherwise affixed to the underlying vessel wall so as to serve and an exovascular scaffold or stent that holds the vessel open in addition to deterring unwanted collapse of the vessel under compressive forces.

FIGS. 12 through 12D show an exovascular support device 500 which is attachable to an outer surface (e.g., the adventitia) of a vein or other anatomical vessel to expand or maintain patency of that vein or other vessel. In this example, the device 500 comprises a resilient patch 502 that is biased to an arcuate cross sectional shape which corresponds to the desired diameter of the vessel on which the patch 502 is to be applied. Optionally, slots 504 may be formed in the patch 502. An adhesive layer 508 is provided on the underside of the patch 502 and, initially, a rigid straightening member 506 is affixed to the upper side of the patch 502 to hold it in a straight, non-arcuate shape, as seen in FIG. 12A. The device 500 is maneuvered into position adjacent to the vessel V to be supported, the vessel is compressed to a flat configuration and the adhesive surface 508 is brought into contact with the vessel wall so as to adhere thereto, as seen in FIG. 12B. Thereafter, the rigid straightening member 506 is removed, allowing the patch 502 to resiliently assume its arcuate configuration which in turn causes the wall of the vessel V to assume the same arcuate shape, as seen in FIGS. 12C and 12D. The patch 502 may be formed of any suitable resilient material, such as polyurethane, stainless steel or nickel-titanium and the adhesive 508 may comprise any suitable, biologically compatible adhesive such as cyanoacrylate.

Figure 13:
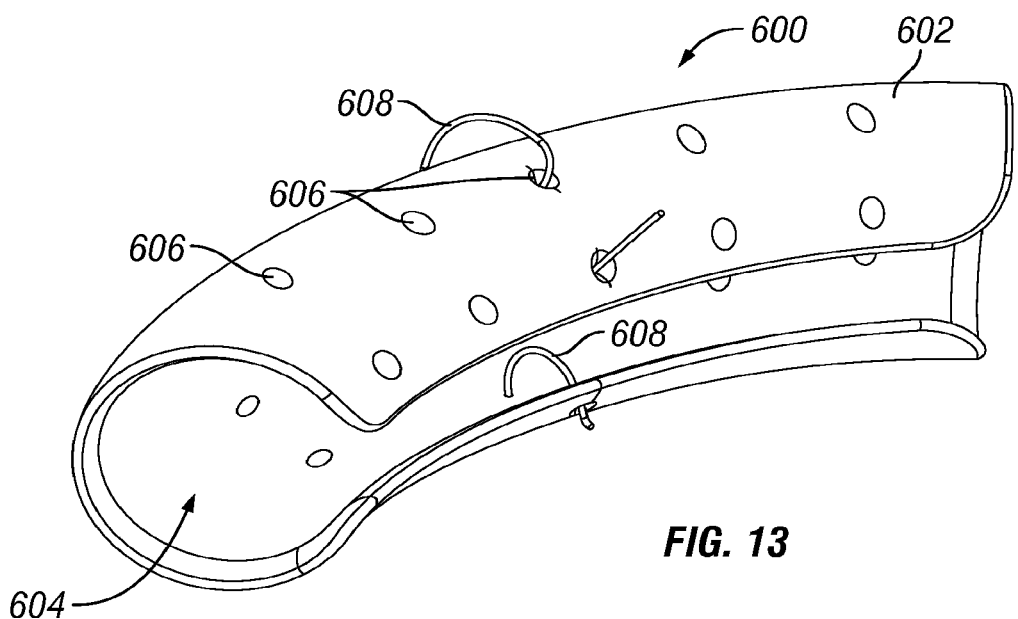
FIG. 13 shows another exovascular device of the present invention.

FIG. 13 shows another exovascular support device 600. This device 600 comprises a rigid shell 602 having suture holes 606 formed therein and having a hollow channel 604 extending therethrough. The shell 602 has a generally arcuate cross sectional shape that corresponds to the desired shape or diameter of the blood vessel to be supported. After the shell 602 has been placed over the blood vessel, suture(s) 608 are passed through holes 606 to suture the underlying portions of the vessel wall to the shell 602. The shell 602 may be formed of any suitable rigid material, such as polyurethane, stainless steel or nickel-titanium.

Figure 14:
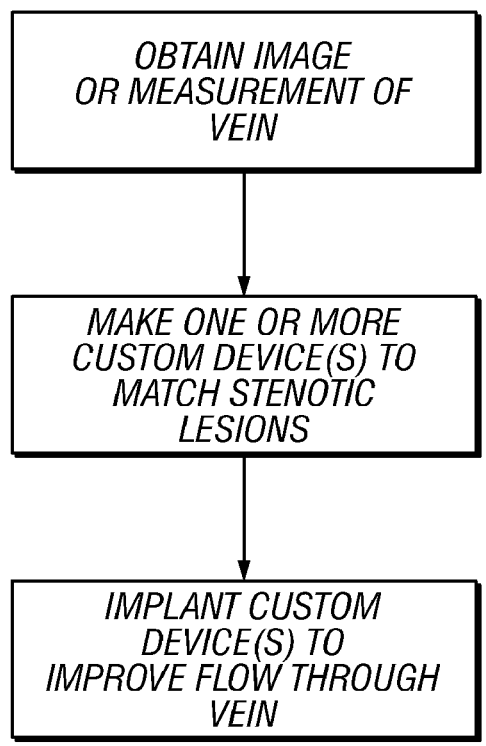
FIG. 14 is a flow diagram showing steps in a method of the present invention wherein a custom-made endovascular and/or exovascular device is used to treat stenosis or stenoses of a particular vein.

As seen in the foregoing examples, the devices of the present invention may be used to practice novel methods whereby a stent, exovascular support or other implantable device is customized, or custom-expanded to accommodate specific regions of stenosis in a vessel, which regions of stenosis may vary in size, location and severity. FIG. 14 is a flow diagram which generally illustrates such a method, which may be useable for treatment of CSVI or other disorders. In this method, an image or measurement of the vein (or other vessel) is taken to ascertain the size, location and severity of each stenotic region (i.e., the "stenosis pattern"). Thereafter one or more custom devices are prepared for treatment of the specific stenotic pattern that was imaged or measured. Such devices may comprise endovascular or exovascular implants having scaffolds, rings or other support structures of appropriate size and having appropriate space therebetween to match the stenosis pattern. Thereafter, the device(s) is/are implanted to improve flow through the vein (or other vessel). As explained above, the step of implanting the device(s), may include selectively expanding different regions of the device(s) to different diameters so as to exert different forces on different stenotic areas, thereby optimizing the improvement of blood flow.

Figure 15A:
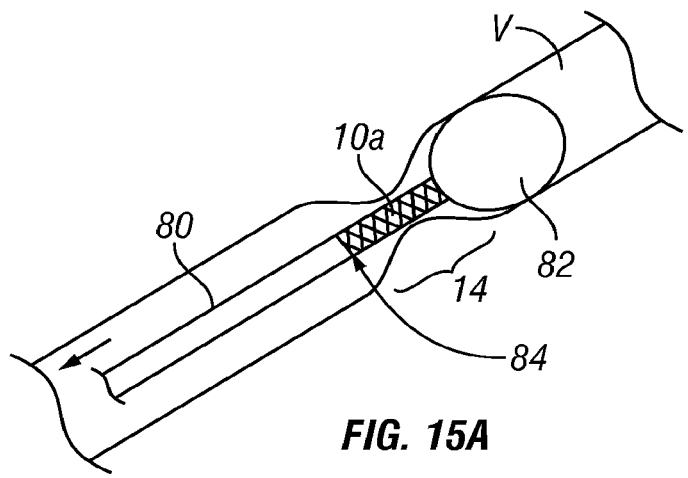
FIGS. 15A through 15C show devices of the present invention and steps in a method of the present invention for implantation of the devices within discrete stenotic region(s) of a vein.
Figure 15B:
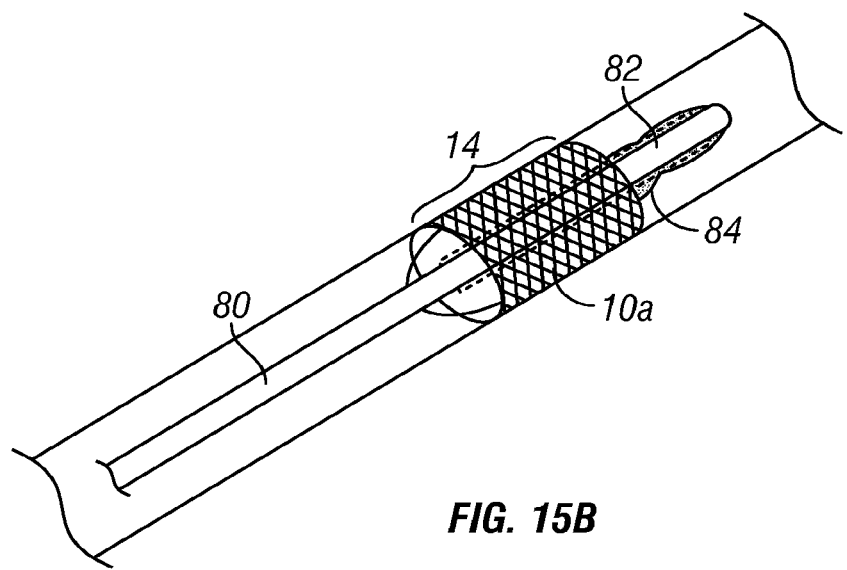
Figure 15C:
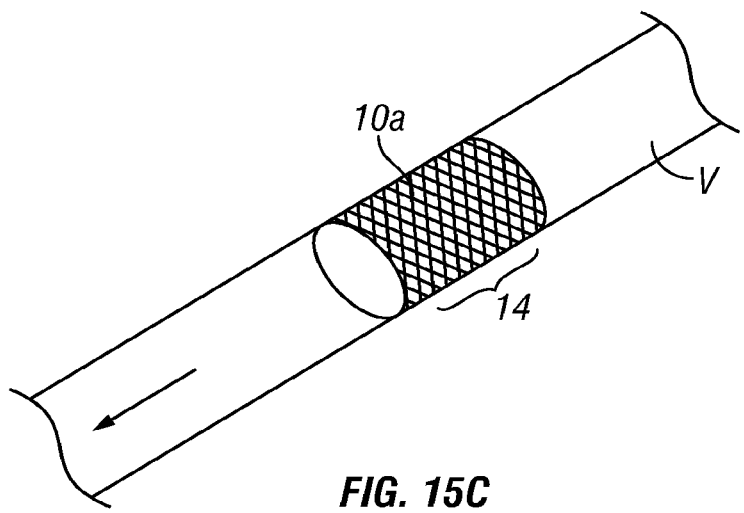

FIGS. 15A and 15B show a delivery device useable for facilitating placement of an endovascular device (e.g., stent) within a stenotic region 14 of a vein V or other body lumen. This delivery device comprises a delivery catheter 80 having a locator balloon 82 located distal to the location at which an endovascular device 10*a* is mounted on the delivery catheter. In cases where the device 10*a* is pressure-expandable, the delivery catheter 80 can incorporate a second balloon positioned under the device 10*a* for pressure-expanding the device 10*a*. In cases where the endovascular device being delivered is self-expanding, the delivery catheter 80 can incorporate a moveable sheath, clip or other restraining member for holding the device 10*a* in a constrained state until it is desired to allow the device 10*a* to self-expand. In cases where the device is both self-expanding and pressure expandable (such as, for example, the embodiments 10*a*-3, 10*a*-4 and 10*a*-5 described above), the delivery catheter 80 can incorporate a moveable sheath, clip or other restraining member as well as a balloon for expanding the device 10*a*. Initially, with the locator balloon 82 in a deflated state and the device 10*a* in a collapsed configuration, the catheter 80 is advanced through the vein V to a position where the locator balloon 82 has passed through the stenotic region 14. Thereafter, the locator balloon 82 is inflated and the catheter 80 is pulled back until resistance is felt indicating that the locator balloon 82 is abutting against the stenotic region 14, thereby indicating that the endovascular device 10*a* is properly positioned within the stenotic region 14. Thereafter, the device 10*a* is allowed or caused to expand, thereby dilating the stenotic region 14. Thereafter, the locator balloon 82 is deflated and the catheter 80 is removed, leaving the endovascular device 10*a* within the stenotic region 14 of the vein V, as seen in FIG. 8C.

Figure 16A:
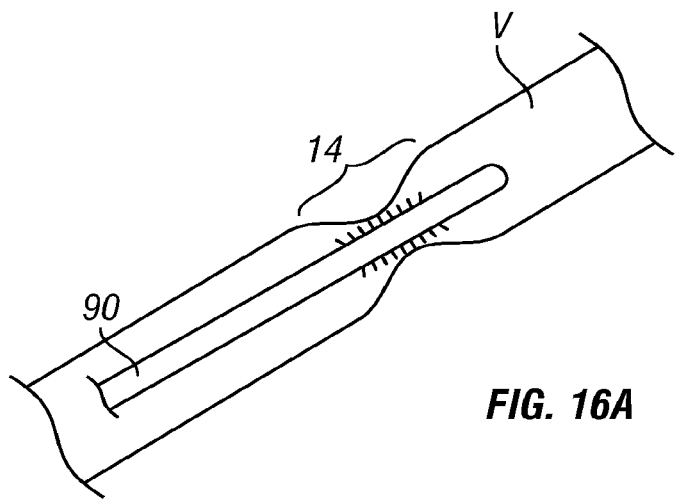
FIGS. 16A and 16B show steps in a method of the present invention wherein energy is applied to a stenotic region of a vein to denature or otherwise affect tissue of the vein in a manner that results in a widening of the vein lumen in the stenotic region.
Figure 16B:
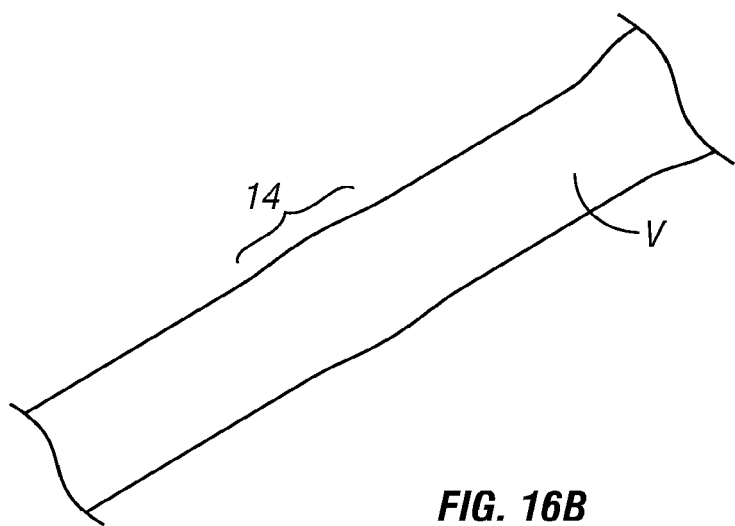

FIGS. 16A and 16B show a method of the present invention wherein an energy emitting device, such as a catheter that delivers energy to the vein wall, is used to thermally, sonically, ultrasonically, or by other means denature, shrink, contract or otherwise cause movement of tissue located in or adjacent to the wall of the vein V, or obstructive matter located within the vein V, in a manner that improves flow through the stenotic region 14. The types of energy that can be delivered include but are not limited to heat, light, laser light, infrared light, a plasma field, sound, ultrasound, electromagnetic radiation, ionizing radiation, etc. For example, in some cases, a balloon catheter having a heated or other energy-emitting balloon could be advanced into the vein V and the balloon inflated so that it contacts or is close to the vein wall and/or obstructive matter in the stenotic region 14 and delivers thermal or other energy via the balloon to cause the desired shrinkage or other movement of the vessel wall and/or obstructive matter. In other cases, other types of energy-delivering catheters may be used. Non-limiting examples of energy-delivering catheters that may be useable or readily modifiable for this purpose include but are not limited to those described in U.S. Pat. No. 5,005,180 (Edelman, et al.) entitled Laser Catheter System; U.S. Pat. No. 5,032,123 (Katz, et al.) entitled Laser Catheter With Radially Divergent Treatment Beam; U.S. Pat. No. 5,417,689 (Fine) entitled Thermal Balloon Catheter And Method; U.S. Pat. No. 5,415,564 (Daikuzono) entitled Laser Balloon Catheter, U.S. Pat. No. 6,048,299 (Hoffman) entitled Radiation Delivery Catheter U.S. Pat. No. 6,176,821 (Crocket, et al.) entitled Radiation Delivery Balloon Catheter U.S. Pat. No. 6,224,590 (Daikuzono) entitled Laser Balloon Catheter U.S. Pat. No. 6,496,737 (Rudie et al.) entitled Thermal Therapy Catheter, U.S. Pat. No. 6,952,615 (Satake) entitled Radiofrequency Thermal Balloon Catheter, U.S. Pat. No. 6,699,170 (Crocket, et al.) entitled Radiation Delivery Balloon Catheter U.S. Pat. No. 7,288,087 (Winston, et al.) entitled Expandable Laser Catheter, the entire disclosure of each such patent being expressly incorporated herein by reference. Alternatively or additionally, in same cases, an energy-emitting implant is implanted within the stenotic region 14 and that implant delivers the desired dose of treatment-effecting energy to the vein wall and/or obstructive matter over a desired time period. Non-limiting examples of energy emitting vascular implants that may be useable or readily modifiable for this purpose are described in U.S. Pat. No. 6,261,320 (Tam et al.) entitled Radioactive Vascular Liner, the entire disclosure of which is also incorporated herein by reference.

FIG. 10A shows an endovascular pumping device that comprises a housing or frame 94a and pump apparatus P for pumping blood through a stenotic region 14 of the vein V, thereby increasing the amount of blood that flows through the stenotic region 14 and consequently lowering venous pressures upstream of the stenotic region 14. The housing or frame can comprise a stent or stent like device that is implantable within the lumen of the vein V. The pump apparatus P includes a power source and at least one pumping member. Non-limiting examples of pump apparatus and implantation techniques that are useable or readily modifiable for this purpose include but are not limited to those described in U.S. Pat. No. 5,676,651 (Larsen Jr., et al.) entitled Surgically Implantable Pump Arrangement And Method For Pumping Body Fluids; U.S. Pat. No. 7,011,620 (Siess) entitled Guidable Intravascular Blood Pump And Related Methods; U.S. Pat. No. 7,022,100 (Abul-Hosn, et al.) entitled Guidable Intravascular Blood Pump And Related Methods; U.S. Pat. No. 7,462,019 (Allarie et al.) entitled Implantable Centrifugal Blood Pump With Hybrid Magnetic Bearings, the entire disclosure of each such patent being expressly incorporated herein by reference.

Figure 17A:
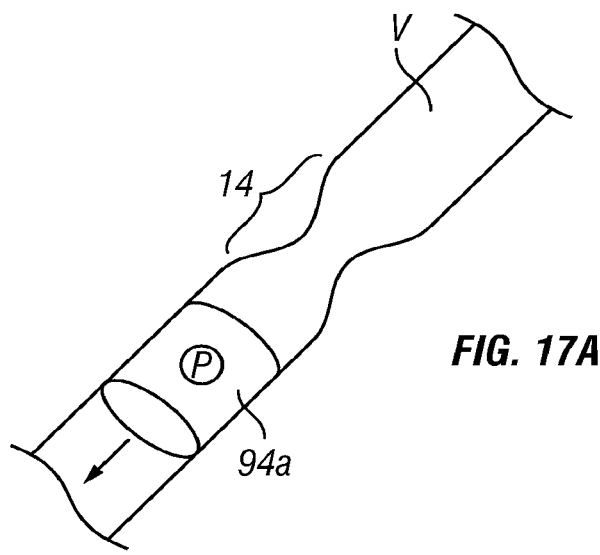
FIG. 17A shows another embodiment of an endovascular device of the present invention comprising a pump for pumping blood through a stenotic region of a vein.
Figure 17B:
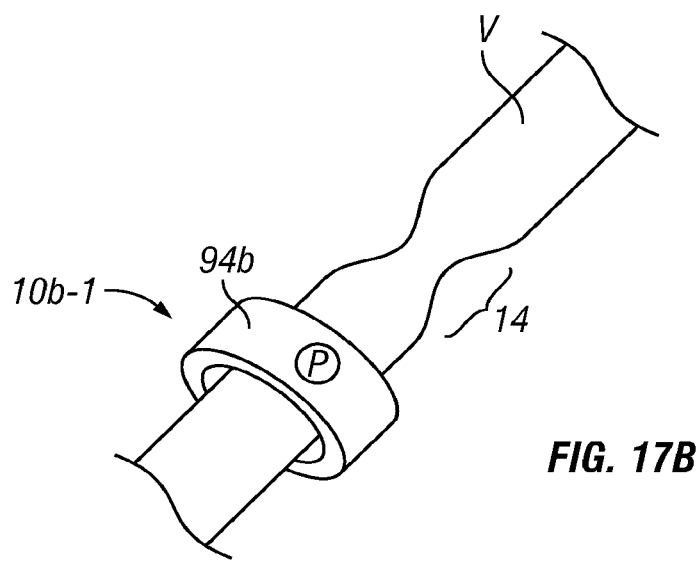
FIG. 17B shows another embodiment of an exovascular device of the present invention comprising a pump for pumping blood through a stenotic region of a vein.
Figure 17C:
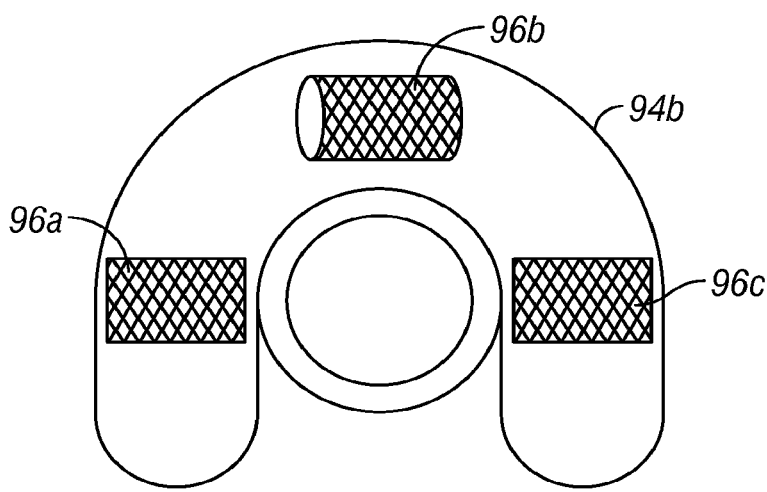
FIG. 17C is an end view of the exovascular pump device of FIG. 17.
Figure 17D:
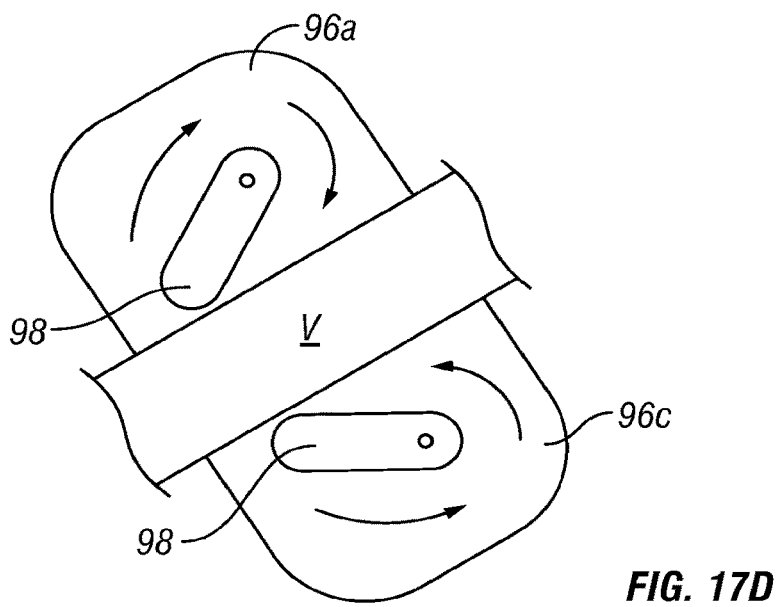
FIG. 17D is a schematic diagram showing one type of pumping apparatus that may be incorporated into an exovascular pump device of the type shown in FIGS. 17C and 17D.

FIGS. 17B-17D show an exovascular device embodiment 10b-1 which comprises a housing or frame 94b and pump apparatus P for pumping blood through a stenotic region 14 of a vein. The housing or frame comprises a collar that fully or partially surrounds the vein V as shown or any other suitable frame or housing that is implanted near the vein and hold the pump apparatus P in the desired position. The pump apparatus P includes a power source and at least one pumping member. As seen in FIG. 17D, in this example, the pump apparatus P has two rotating cam members 98 which, when rotating, compress the wall of the vein V in a peristaltic fashion, thereby propelling blood through the lumen of the vein and speeding the rate at which blood flows through the stenotic region 14.

In any of the embodiments having a pump apparatus P, the pump apparatus P may operate continuously or non-continuously. In embodiments where the pump apparatus P is intended to operate non-continuously, it can be connected to or in communication with a sensor of any type described here above for sensing a variable (e.g., blood pressure, posture, respiratory cycle, etc.) and causing the pump to actuate when that variable exceeds some predetermined limit or range.

Figure 18A:
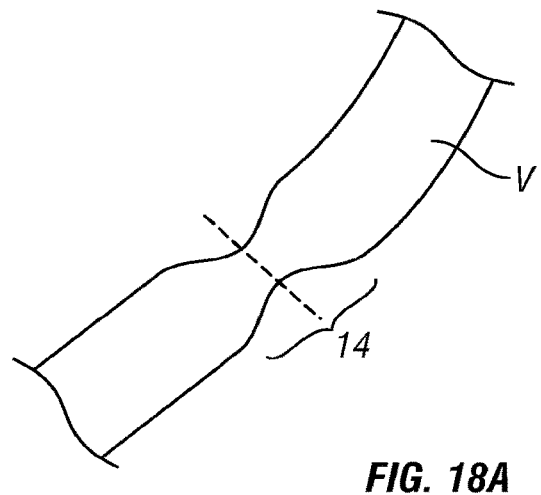
FIGS. 18A and 18B show steps in a method for treating stenosis of a vein by transecting the vein at the site of a stenosis and subsequently creating a flow-through anastomosis between the transected vein segments.
Figure 18B:
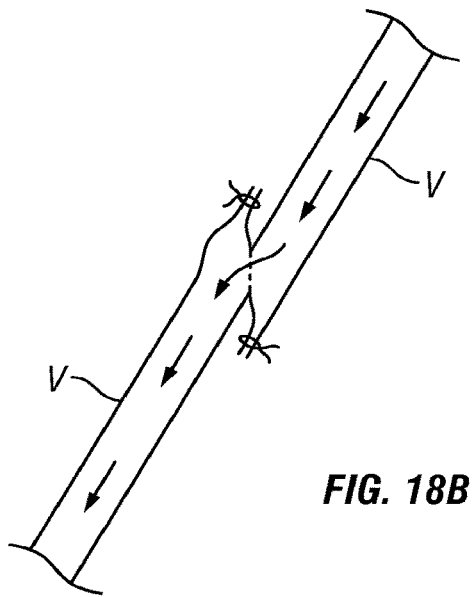

FIGS. 18A and 18B show a method for treating stenosis of a vein V having a stenotic region 14. In this method, the vein V is transected through the stenotic region 14 at the location indicated by the dotted line on FIG. 18A. The transected ends of the vein V are then ligated and the vein segments are anastomosed at non-stenotic locations as seen in FIG. 18B. In this particular example, the vein segments are anastomosed in side-to-side fashion. This procedure may be performed by open surgery using conventional surgical technique or by a minimally-invasive endoscopic technique (e.g., creating a cavity within tissue adjacent to the vein V and inserting an endoscope and operative instruments into that tissue cavity or by a translumninal catheter-based technique) or transluminally using catheter-based devices. Examples of devices and methodology that may be used to perform this procedure by minimally-invasive or transluminal techniques include but are not limited to those described in U.S. Pat. No. 5,549,122 (Detweilwer) entitled Methods Of Surgical Mammalian Vessel Anastomosis; U.S. Pat. No. 6,071,292 (Makower, et al.) entitled Transluminal Methods And Devices For Closing, Forming Attachments To, And/Or Forming Anastomotic Junctions In, Luminal Anatomical Structures; U.S. Pat. No. 6,231,587 (Makower) entitled Devices For Connecting Anatomical Conduits Such As Vascular Structures; U.S. Pat. No. 6,579,311 (Makower) entitled Device System and Method for Interstitial Transvascular Intervention; U.S. Pat. No. 6,616,675 (Evard, et al.) entitled Methods And Apparatus For Connecting Openings Formed In Adjacent Blood Vessels Or Other Anatomical Structures; U.S. Pat. No. 7,056,325 (Makower, et al.) entitled Transluminal Methods And Devices For Closing, Forming Attachments To, And/Or Forming Anastomotic Junctions In, Luminal Anatomical Structures; U.S. Pat. No. 7,220,268 (Blatter) entitled Methods For Anastomosis Of A Graft Vessel To A Side Of A Receiving Vessel; U.S. Pat. No. 7,618,427 (Ortiz et al.) entitled Device And Method For Intralumenal Anastomosis, the entire disclosure of each such application being expressly incorporated herein by reference.

Figure 19A:
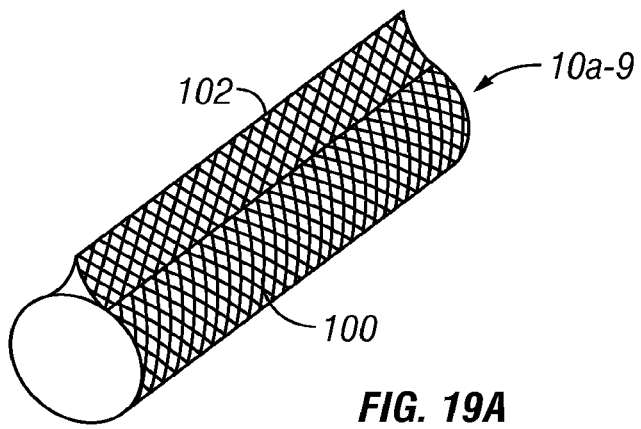
FIG. 19A shows another embodiment of an endovascular device of the present invention comprising a cutting surface which forms a full-thickness or partial-thickness cut in the wall of the vein so as to relieve constraining tissue or otherwise facilitate enlargement of a stenotic region of the vein.
Figure 19B:
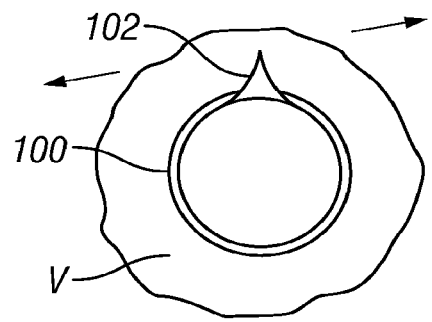
FIG. 19B is a cross sectional view of a vein having the device of FIG. 12A implanted therein.

FIGS. 19-19B show an endovascular device embodiment 10a-9 comprising a self-expanding and/or pressure expandable cutting stent comprising a radially expandable stent body 100 and a cutting blade 102. As shown in FIG. 12B, when this device is implanted within a vein V the cutting blade 102 will form a full-thickness or partial-thickness cut in the wall of the vein V, thereby relieving a stricture caused by constraining tissue or to otherwise facilitate enlargement of a stenotic region 14 of the vein V. As an alternative, the cutting blade can be located on a balloon or a balloon catheter that is inserted into the vein V and used to firm a full or partial thickness incision. Although the embodiment shown in this example has a straight, longitudinally-extending cutting blade 102, it is to be understood that various other cutting blades (e.g., transverse, circumferential, helical, etc.) can be used. The stent body 100 is of a suitable design and comprises any of the stents described herein including the endovascular device embodiments 10a-1, 10a-2 and 10a-3 described above. Examples of other cutting stents, cutting balloons and methods that are useable, or readily modifiable for, this purpose include but are not limited to those described in U.S. Pat. No. 5,713,913 (Lary, et al.) entitled Device And Method For Transecting A Coronary Artery; U.S. Pat. No. 6,036,708 (Sciver) entitled Cutting Stent With Flexible Tissue Extractor, U.S. Pat. No. 7,070,576 (O'Brien et al.) entitled Directional Cutting Balloon; U.S. Pat. No. 7,131,981 (Appling, et al.) entitled Device And Method For Converting A Balloon Catheter Into A Cutting Balloon Catheter, U.S. Pat. No. 7,291,158 (Crow, et al.) entitled Cutting Balloon Catheter Having A Segmented Blade; U.S. Pat. No. 7,279,002 (Shaw, et al.) entitled Cutting Stent And Balloon; U.S. Pat. No. 7,303,572 (Melsheimer, et al.) entitled Catheter Assembly With Plaque Cutting Balloon; U.S. Pat. No. 7,396,358 (Appling, et al.) entitled Device And Method For Converting A Balloon Catheter Into A Cutting Balloon Catheter and U.S. Pat. No.

7,632,288 (Wu) entitled Cutting Balloon Catheter With Improved Pushability, the entire disclosure of each such patent being expressly incorporated herein by reference.

Figure 20A:
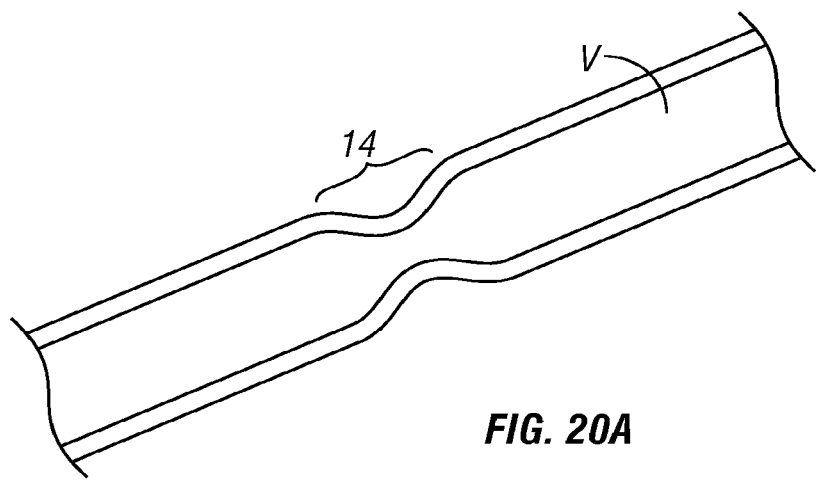
FIGS. 20A and 20B show another method and embodiment of an exovascular device of the present invention comprising a spring that pulls outwardly on anchors embedded in or attached to the vein so as to dilate a stenotic region of the vein.
Figure 20B:
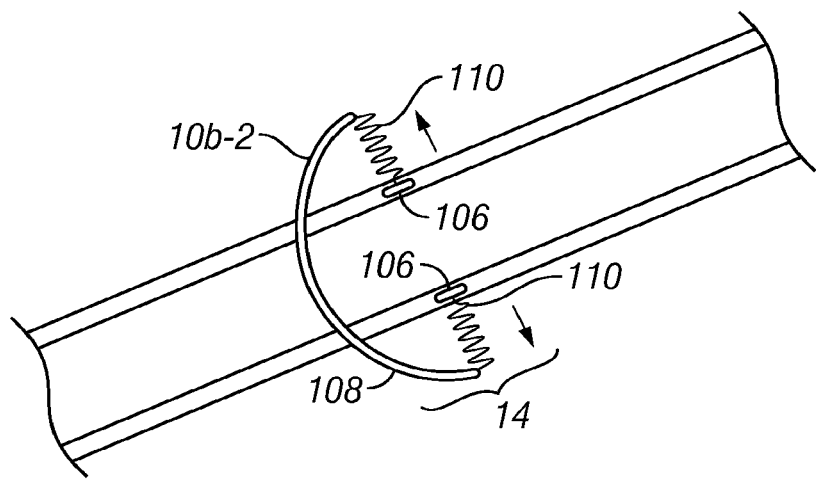

FIGS. 20A and 20B show an exovascular device embodiment 10b-2 that widens a stenotic region 14 of a vein V by pulling outwardly on the wall of the vein V at or near the stenotic region 14. In the example shown, this exovascular device embodiment 10b-2 comprises anchors 106 that embed in or attach to the vein wall, an exovascular frame 108 and cinching members (e.g., springs) which connect the anchors 106 to the frame 108 and pull outwardly on the anchors 106 to expand or widen the stenotic region 14 of the vein V. The anchors 106 comprise sutures, wires, hooks, barbed objects or other members that are embedded in or otherwise engage the tissue, or they comprise members that are affixed to the vein wall by adhesive, sutures or other suitable means. The cinching members 110 comprise springs or plastically deformable members that become plastically deformed by a surgeon's hand or by inflation of a balloon within the vein V or by any other suitable means to provide the desired amount of tension on the anchors 106. Examples of tissue anchors, cinching members and other apparatus/methods that are useable, or readily modifiable for, this purpose include but are not limited to those described in U.S. Pat. No. 5,380,334 (Torrie, et al.) entitled Soft Tissue Anchors And Systems For Implantation; U.S. Pat. No. 5,601,558 (Torrie, et al.) entitled Soft Tissue Anchors And Systems For Implantation; U.S. Pat. No. 7,390,329 (Westra, et al.) entitled Methods For Grasping And Cinching Tissue Anchors and United States Patent Application Publication Nos. 2008/0033488 (Catanese, Joseph III, et al.) entitled Devices, Systems And Methods For Retracting, Lifting, Compressing, Supporting Or Repositioning Tissues Or Anatomical Structures, the entire disclosure of each such patent and published patent application being expressly incorporated herein by reference.

In another embodiment, the endovascular device is a helical coil made of a zig-zag shaped wire. The helical coil provides overall compliance along the length of the device. The zig-zag shaped wire provides opposition to the vein wall. The device can be plastically expanded to various diameters by balloon dilation along its length.

Any of the devices of the present invention may contain or be coated with an active substance for providing some desired therapeutic effect. In cases where the device is being used to improve flow through a stenotic vein (such as in cases where the device is being implanted to treat CCVI), the active substance may comprise a substance that causes venodilation, limit venocontraction or otherwise increases bloodflow through the vein. Examples of such substances include but are not limited to: nitrates, nitroglycerin, nitric oxide (NO), isosorbide dinitrate, isosorbide mononitrate, phosphodiesterase inhibitors, calcium channel blockers, inhibitors of $Ca^{2+}$ influx, glyceryl trinitrate, angiotensin converting enzyme (ACE) inhibitors, angiotensin II receptor blockers (ARBs), aldosterone blockers, nesiritide, etc.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified, if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. Additionally, unless otherwise indicated, where an example or embodiment having certain components, steps or elements is described herein, that example or embodiment may, in at least some but not necessarily all cases, consist essentially of just those described components, steps or elements to the substantial exclusion of others, should Applicant choose to claim the invention in such manner. All reasonable additions, deletions, modifications and alterations to the examples and embodiments described herein are to be considered equivalents of the described examples and embodiments and are to be included within the scope of the following claims.

What is claimed is:

1. A method for treating a rising venous backpressure due to an intrathoracic pressure that affects venous outflow through a cerebrospinal vein involving a stent device comprising:
   providing at least one self-expanding stent member configured to be placed within a right internal jugular vein;
   configuring the at least one self-expanding stent member within the right internal jugular vein to apply a non-continuous force on the right internal jugular vein, the at least one self-expanding stent member having a first applied force;
   providing the at least one self-expanding stent member with a sensor and configuring the sensor to sense a physiological triggering variable, the physiological triggering variable being a rising venous backpressure due to an intrathoracic pressure that affects venous outflow through a cerebrospinal vein;
   providing the at least one self-expanding stent member with a microprocessor and configuring the microprocessor to automatically actuate the at least one self-expanding stent member to apply a second applied force that is different from the first applied force when the sensor senses the physiological triggering variable;
   providing at least one deformable constraining member connected to the at least one self-expanding stent member;
   wherein the at least one self-expanding stent member being initially deployable in a collapsed configuration and thereafter self-expandable to a first expanded configuration, the at least one deformable constraining member being operative to diametrically constrain the at least one self-expanding stent member so that it does not self expand beyond the first expanded configuration; and
   wherein all or part of the at least one deformable constraining member being thereafter deformable to a deformed configuration that allows all or part of the at least one self-expanding stent member to further expand to a second expanded configuration, the second expanded configuration of the at least one self-expanding stent configured to exert a varying force in response to information provided by the sensor to the microprocessor.

2. The method of claim 1 wherein the at least one self-expanding stent member comprises one or more self-expanding rings.

3. The method of claim 1 wherein the at least one self-expanding stent member comprises one or more self-expanding zig-zag rings.

4. The method of claim 1 wherein the at least one self-expanding stent member comprises one or more self-expanding mesh rings.

5. The method of claim 1 wherein the at least one deformable constraining member comprises one or more deformable filaments.

6. The method of claim 1 wherein the at least one deformable constraining member comprises one or more deformable bands.

7. The method of claim 1 wherein the at least one deformable constraining member comprises at least one deformable sheaths that is configured to define a tube extending a length of the stent device.

8. The method of claim 7 wherein the at least one deformable sheath comprises an inner polymer layer and an outer polymer layer and wherein the least one self-expanding stent member is positioned between the inner and outer polymer layers.

9. The method of claim 7 wherein the at least one deformable sheath has perforations formed therein.

10. The method of claim 9 wherein the size, shape, number and location of the perforations are selected to provide desired amounts of flexibility and diametric constraint.

11. The method of claim 9 wherein the perforations are round.

12. The method of claim 9 wherein the perforations are polygonal.

13. The method of claim 1 wherein the at least one deformable constraining member is formed at least in part by a deformable metal or polymer.

14. The method of claim 13 wherein a pressure deformable metal or polymer is selected from the group consisting of: PTFE, ePTFE, polyurethane, stainless steel or nickel-titanium.

15. The method of claim 1 wherein the at least one self-expanding stent member comprises a plurality of self-expanding ring members and wherein the at least one deformable constraining member comprises a plurality of deformable constraining members that, in addition to providing diametric constraint, connect the plurality of self-expanding ring members to one another in series.

16. The method of claim 15 wherein the plurality of self-expanding ring members comprise zig-zag rings having apices and wherein, in addition to providing diametric constraint, the deformable constraining members connect apices of one self-expanding zig-zag ring member to apices of another self-expanding zig-zag ring member.

* * * * *